US010426800B2

(12) United States Patent
Lin et al.

(10) Patent No.: US 10,426,800 B2
(45) Date of Patent: Oct. 1, 2019

(54) ADIPOSE TISSUE-DERIVED STEM CELLS FOR VETERINARY USE

(71) Applicant: CELL4VET CORPORATION, San Mateo, CA (US)

(72) Inventors: Ching Shwun Lin, San Mateo, CA (US); Tom F. Lue, Hillsborough, CA (US); Guiting Lin, San Francisco, CA (US)

(73) Assignee: CELL4VET CORPORATION, San Mateo, CA (US)

( * ) Notice: Subject to any disclaimer, the term of this patent is extended or adjusted under 35 U.S.C. 154(b) by 57 days.

(21) Appl. No.: 15/700,604

(22) Filed: Sep. 11, 2017

(65) Prior Publication Data
US 2018/0021381 A1 Jan. 25, 2018

Related U.S. Application Data

(60) Continuation of application No. 14/858,210, filed on Sep. 18, 2015, now Pat. No. 9,757,421, which is a division of application No. 12/997,067, filed as application No. PCT/US2009/046587 on Jun. 8, 2009, now Pat. No. 9,144,584.

(60) Provisional application No. 61/060,701, filed on Jun. 11, 2008, provisional application No. 61/168,148, filed on Apr. 9, 2009.

(51) Int. Cl.
*A61K 35/28* (2015.01)
*A61K 9/16* (2006.01)
*C12N 5/0775* (2010.01)
*A61K 9/00* (2006.01)
*A61K 47/34* (2017.01)
*A61K 35/12* (2015.01)

(52) U.S. Cl.
CPC ............ *A61K 35/28* (2013.01); *A61K 9/0019* (2013.01); *A61K 9/0024* (2013.01); *A61K 9/0034* (2013.01); *A61K 9/1647* (2013.01); *A61K 9/1652* (2013.01); *A61K 35/12* (2013.01); *A61K 47/34* (2013.01); *C12N 5/0667* (2013.01); *C12N 2500/84* (2013.01); *C12N 2531/00* (2013.01); *C12N 2533/40* (2013.01); *C12N 2533/78* (2013.01)

(58) Field of Classification Search
None
See application file for complete search history.

(56) References Cited

U.S. PATENT DOCUMENTS

| | | |
|---|---|---|
| 4,298,002 A | 11/1981 | Ronel |
| 4,789,734 A | 12/1988 | Pierschbacher |
| 4,792,525 A | 12/1988 | Ruoslahti |
| 4,879,237 A | 11/1989 | Ruoslahti |
| 4,892,538 A | 1/1990 | Aebischer et al. |
| 4,988,621 A | 1/1991 | Ruoslahti |
| 5,011,472 A | 4/1991 | Aebischer et al. |
| 5,308,701 A | 5/1994 | Cohen |
| 5,837,234 A | 11/1998 | Gentile et al. |
| 5,965,997 A | 10/1999 | Alwardi |
| 7,888,892 B2 | 2/2011 | McReynolds et al. |
| 2006/0147430 A1 | 7/2006 | Sayre et al. |
| 2006/0210532 A1* | 9/2006 | Carmeliet ............ A61K 31/203 424/85.1 |
| 2010/0124563 A1 | 5/2010 | Coleman et al. |

FOREIGN PATENT DOCUMENTS

| | | | |
|---|---|---|---|
| WO | 9110425 A1 | 7/1991 | |
| WO | 9110470 A1 | 8/1991 | |
| WO | 2005035742 A2 | 4/2005 | |
| WO | WO-2005035742 A2 * | 4/2005 | ........... C12N 5/0667 |

OTHER PUBLICATIONS

Williams, Kellie J; et al; "Isolation and Characterization of Porcine Adipose Tissue-Derived Adult Stem Cells" Cells Tissues Organs, 188, 251-258, 2008 (Year: 2008).*
Gronthos, et al., "Surface Protein Characterization of Human Adipose Tissue-Derived Stromal Cells", J. Cellular Physiology, Oct. 2001; 189(1):54-63.
Valina et al., "Intracoronary administration of autologous adipose tissue-derived stem cells improves left ventricular function, perfusion, and remodelling after acute myocardial infarction", European Heart Journal (2007), 28:2667-2677.
Zuk et al., "Multilineage Cells from Human Adipose Tissue Implications for Cell-Based Therapies", Tissue Engineering (2001), 7:211-228.
Burris et al., "A Novel Method for Analysis of Nuclear Receptor Function at Natural Promoters: Peroxisome Proliferator-Activated Receptor v Agonist Actions on aP2 Gene Expression Detected Using Branched DNA Messenger RNA Quantitation", Molecular Endocrinology (1999), 13:410-417.
Erickson et al., "Chondrogenic Potential of Adipose Tissue-Derived Stromal Cells in Vitro and in Vivo", Biochemical & Biophysical Research Communications (2002), 290:763-769.
Halvorsen, et al., "Thiazolidinediones and Glucocorticoids Synergistically Induce Differentiation of Human Adipose Tissue Stromal Cells: Biochemical, Cellular, and Molecular Analysis", Metabolism (2001), 50:407-413.
Halvorsen, et al., "Extracellular Matrix Mineralization and Osteoblast Gene Expression by Human Adispose Tissue-Derived Stromal Cells", Tissue Engineering (2001), 7(6):729-741.
Harp, et al., "Differential Expression of Signal Transducers and Activators of Transcription during Human Adipogenesis", Biochemical and Biophysical Research Communications (2001), 281:907-912.
Saladin et al., "Differential Regulation of Peroxisome Proliferator Activated Receptor v1 (PPARv1) and PPARv2 Messenger RNA Expression in the Early Stages of Adipogenesis1", Cell Growth & Differentiation (1999), 10:43-48.
Sen, et al., "Adipogenic Potential of Human Adipose Derived Stromal Cells From Multiple Donors is Heterogeneous", J. of Cellular Biochemistry (2001), 81:312-319.

(Continued)

*Primary Examiner* — David W Berke-Schlessel
(74) *Attorney, Agent, or Firm* — Myers Wolin, LLC

(57) ABSTRACT

The invention provides for compositions and methods for making and using adipose-derived stem cells for treating non-human mammals for various medical conditions.

11 Claims, 25 Drawing Sheets

(56) References Cited

OTHER PUBLICATIONS

Zhou et al., "Analysis of the pattern of gene expression during human adipogenesis by DNA microarray", Biotechnology Techniques (1999), 13:513-517.
Hauner, et al., "Promoting Effect of Glucocorticoids on the Differentiation of Human Adipocyte Precursor Cells Cultured in a Chemically Defined Medium", J. Clin. Invest. (1989), 84:1663-1670.
Rodbell, et al., "Metabolism of Isolated Fat Cells", J. Biological Chemistry (1966), 241(1):130-139.
Fotuhi P., et al., "Electrophysiological consequence of adipose-derived stem cell transplantation in infarcted porcine myocardium", Europace (2007), 9(12):1218-1221.
Madonna R. et al., "Myocardin A Enhances Telomerase Activities in Adipose Tissue Mesenchymal Cells and Embryonic Stem Cells Undergoing Cardiovascular Myogenic Differentiation", Stem Cells (2008), www.stemcells.com, 26(1):202-211.
Qu CQ, et al., "Osteogenic and adipogenic potential of porcine adipose mesenchymal stem cells", In Vitro Cell. Dev. Biol.—Animal. (2007), 43(2):95-100.
Wang K.H. et al., "Optimizing proliferation and characterization of multipotent stem cells from porcine adipose tissue", Biotechnol. Appl. Biochem. (2008), 51:159-166.
Williams K.J., "Isolation and Characterization of Porcine Adipose Tissue-Derived Adult Stem Cells", Cells Tissues Organs (2008) 188:251-258.
Cao et al., "High Glucose Is Necessary for Complete Maturation of Pdx1-VP16-Expressing Hepatic Cells into Functional Insulin-Producing Cells", Diabetes (2004), 53:3168-3178.
Tang et al., "Reprogramming liver-stem WB cells into functional insulin-producing cells by persistent expression of Pdx1- and Pdx1-VP16 mediated by lentiviral vectors", Laboratory Investigation (2006), 86:83-93.
Matsumoto et al., "Influences of Preservation at Various Temperatures on Liposuction Aspirates", Plast. Reconstr. Surg. (2007), www.PRSJournal.com, 120(6):1510-1517.
Lin G. et al., "Defining Stem and Progenitor Cells within Adipose Tissue", Stem Cells and Development (2008), 17:1053-1063.
Ning H. et al., "Neuron-like differentiation of adipose tissue-derived stromal cells and vascular smooth muscle cells", Differentiation (2006), 74:510-518.
Cima, et al., "Hepatocyte Culture on Biodegradable Polymeric Substrates", Biotechnololgy and Bioengineering (1991), 38:145-158.
Tang D. et al., "Role of Pax4 in Pdx1-VP16-mediated liver-to-endocrine pancreas transdifferentiation", Laboratory Investigation (2006), 86:829-841.
Kim et al., "The Preventive and Therapeutic Effects of Intravenous Human Adipose-Derived Stem Cells in Alzheimer's Disease Mice", www.plosone.org, (2012), 7(9):-17.
Lin et al., "Adipose-derived Stem Cells for the Treatment of Peyronie's Disease?", Eur Urol (2012), http://dxdoi.org/10.1016/j.eururo.2012.10.049.
Butala, et al., "Endogenous Stem Cell Therapy Enhances Fat Graft Survival", American Society of Plastic Surgeons, www.PRSJournal.com (2012), 293-306.
Marconi et al., "Human Adipose-Derived Mesenchymal Stem Cells Systemically Injected Promote Peripheral Nerve Regeneration in the Mouse Model of Sciatic Crush", Tissue Engineering: Part A (2012), 18(11,12):1264-1272.
Sacerdote P. et al., "Systemic Administration of human Adipose-derived Stem Cells (hASCs) reverts nociceptive hypersensitivity in an experimental model of neuropathy", Stem Cells and Development (2012), 1-12.
Castiglione et al., "Intratunical Injection of Human Adipose Tissue-derived Stem Cells Prevents Fibrosis and Is Associated with Improved Erectile Function in a Rat Model of Peyronie's Disease", Eur Urol (2012), http://dx.doi.org/10.1016/jeururo.2012.09.034.
Li et al, "Do mesenchymal stem cells function across species barriers? Relevance for xenotransplantation", Xenotransplantation (2012), 19:273-285.
Lin et al., "Allogeneic and Xenogeneic Transplantation of Adipose-Derived Stem Cells in Immunocompetent Recipients Without Immunosuppressants", Stem Cells and Development (2012), 21(15):2770-2778.
Horie M. et al, "Intra-articular Injection of human MesenChymal Stem Cells (MSCs) Promote Rat Meniscal Regeneration by Being Activated to Express Indian Hedgehog that Enhances Expression of Type II Collegan", Osteoarthritis Cartilage (2012 ), 20(10):1197-207, doi: 10.1016/j.joca.2012.06.002. Epub Jun. 29, 2012.
Zhang et al., "Comparison of the therapeutic effects of human and mouse adipose-derived stem cells in a murine model of lipopolysac-charide-induced acute lung injury", Stem Cell Research & Therapy 2013, 4:13 doi:10.1186/scrt161.
Thomas Schubert et al., "Galactosyl-knock-out engineered pig as a xenogenic donor source of adipose MSCs for bone regeneration", Biomaterials xxx (2013) 1e11, Jan. 10, 2013.

* cited by examiner

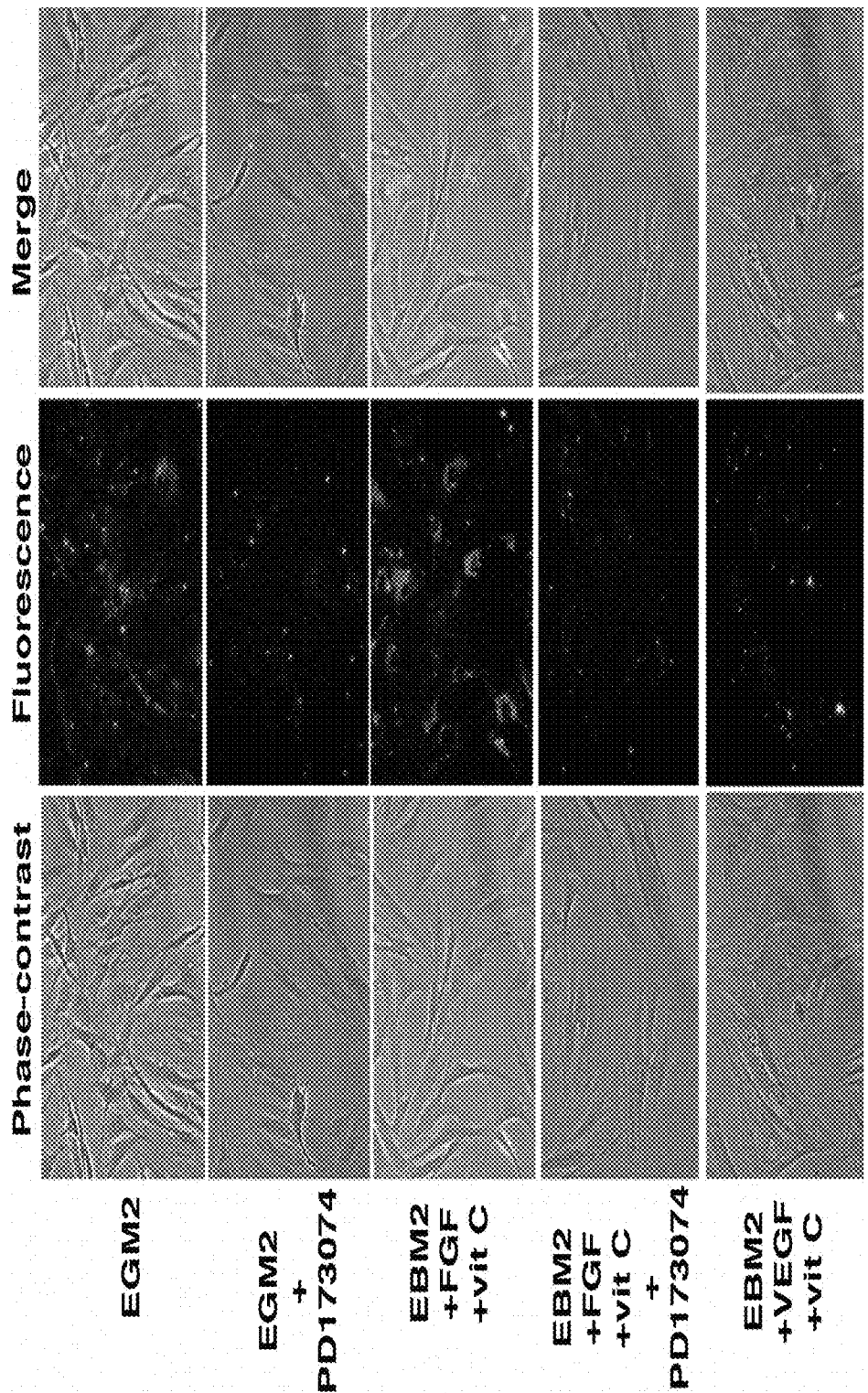

ADIPOSE TISSUE-DERIVED STEM CELLS FOR VETERINARY USE

CROSS-REFERENCE TO RELATED APPLICATIONS

This is a continuation of U.S. application Ser. No. 14/858,210, filed Sep. 18, 2015, which is a divisional of U.S. application Ser. No. 12/997,067 filed Feb. 14, 2011, now U.S. Pat. No. 9,144,584 issued on Sep. 29, 2015, which is a national stage of International Application No. PCT/US2009/046587, filed Jun. 8, 2009, which claims the benefit under 35 U.S.C. § 119 (e) of U.S. Provisional Application No. 61/060,701 filed Jun. 11, 2008, and U.S. Provisional Application No. 61/168,148 filed Apr. 9, 2009, the contents of each which are incorporated herein by reference in their entirety.

FIELD OF THE INVENTION

The invention provides for compositions and methods for making and using adipose-derived stem cells for treating non-human mammals for various medical conditions.

BACKGROUND

The adipose tissue contains a stromal vascular fraction (SVF) from which multipotent cells have been isolated. These cells are variously called processed lipoaspirate (PLA) cells, adipose tissue-derived mesenchymal stem cells, multipotent adipose-derived stem (MADS) cells, adipose tissue-derived stem cells, adipose tissue-derived stromal cells (ADSC, ATSC), adipose tissue derived adult stem (ADAS) cells, adipose tissue-derived adult stromal (ADAS) cells, and adipose tissue-derived cells (ADC).

ADSC possess phenotypes and gene expression profiles similar to those of bone marrow stem cells (BMSC). In addition to having the capacity for self-renewal and long-term growth, ADSC are capable of differentiating into diverse cell types including adipocytes, osteoblasts, chondrocytes, hepatocytes, myocytes, cardiomyocytes, neurons, and epithelial cells. Thus, ADSC are not only increasingly accepted as bona fide adult stem cells but also considered to be superior to other types of adult stem cells for future clinical applications. Whereas bone marrow can only be obtained in limited quantity because of donor site morbidity, the adipose tissue is usually obtainable in abundance, especially in our increasingly obese society. In addition, clonogenic studies have established that the number of BMSC in bone marrow is approximately 1 in 25,000 to 1 in 100,000, whereas the average frequency of ADSC in processed lipoaspirate is approximately 2% of nucleated cells. Thus, the yield of ADSC from 1 g of fat is approximately 5000 cells, whereas the yield of BMSC is 100-1000 cells per milliliter of marrow.

Previous attempts have been made to use ADSC for therapeutic purposes. See, for example, WO 2005/035742. However, these attempts have largely focused on the autologous uses for the ADSC in a veterinary setting. For veterinary clinics, autologous treatment plans are overly time consuming for both the veterinarian and the pet owner. What is needed are compositions and methods for treating non-human mammals, such as pets and farm animals, in a manner that is efficient and does not cause rejection of transplanted cells. The invention described herein provides these advantages and provides additional benefits as well.

All patents, patent applications, references, and other publications disclosed herein are hereby incorporated by reference in their entirety.

SUMMARY

The invention provides for compositions and methods for making and using adipose tissue-derived stem cells (ADSC). In one aspect, the invention provides for methods for treatment of non-human mammals for various medical conditions. In one aspect, the invention provides for methods for treating urinary incontinence in a non-human mammal comprising administering to the non-human mammal an effective amount of adipose tissue-derived stem cells (ADSC). The non-human mammal may also have secondary symptoms wherein the secondary symptom is bladder infection or urinary scalding or both bladder infection and urinary scalding.

In another aspect of the invention, the invention provides for methods for treating inflammatory disease in a non-human mammal comprising administering to the non-human mammal an effective amount of adipose tissue-derived stem cells (ADSC). In one embodiment, the inflammatory disease is arthritis. In another embodiment, the arthritis is osteoarthritis.

In another aspect of the invention, the invention provides for methods for palliating pain in a non-human mammal in need thereof comprising administering to the non-human mammal an effective amount of adipose tissue-derived stem cells (ADSC).

In another aspect of the invention, the invention provides for methods of treating diabetes in a non-human mammal in need thereof comprising administering to the non-human mammal an effective amount of adipose tissue-derived stem cells (ADSC).

In another aspect of the invention, the invention provides for of treating a medical condition in a non-human mammal in need thereof comprising administering to the non-human mammal an effective amount of adipose tissue-derived stem cells (ADSC) wherein the medical condition is one or more condition selected from the group consisting of: urinary incontinence, osteoarthritis, degenerative myelopathy, diabetes, tissue regeneration, wound healing, scarring, soft tissue defect, fecal incontinence, dilated cardiomyopathy, hip dysplasia, avascular necrosis of the femoral head, ligament injury, tendon injury, spinal cord injury, atherosclerosis-related infarctions, arthritis, and muscular dystrophy.

The invention provides for treatment or alleviation of the condition discussed in the method of any one of the above wherein the ADSCs are xenogeneic to the non-human mammal. In one aspect, the treatment is a xenotransplantation with minimal rejection or inflammation from the treatment with ADSCs. In any of the methods described above and herein, the non-human mammal can be any one of the following non-limiting examples: dog, cat, horse, rabbit, pig, monkey, baboon, chimpanzee, orangutan, tiger, lion, bear, cheetah, and llama.

In another aspect, the invention provides for a bank of non-human ADSCs for use in treatment of a medical condition wherein the ADSCs are xenogeneic to the recipient of the ADSCs and wherein the medical condition is one or more condition selected from the group consisting of: urinary incontinence, osteoarthritis, degenerative myelopathy, diabetes, tissue regeneration, wound healing, scarring, soft tissue defect, fecal incontinence, dilated cardiomyopathy, hip dysplasia, avascular necrosis of the femoral head, ligament injury, tendon injury, spinal cord injury, atherosclerosis-related infarctions, arthritis, and muscular dystrophy.

In another aspect, the invention provides for a bank of non-human ADSC for use in treatment of a medical condition wherein the ADSCs are allogeneic to the recipient of the ADSC and wherein the medical condition is one or more condition selected from the group consisting of: urinary incontinence, osteoarthritis, degenerative myelopathy, diabetes, tissue regeneration, wound healing, scarring, soft tissue defect, fecal incontinence, dilated cardiomyopathy, hip dysplasia, avascular necrosis of the femoral head, ligament injury, tendon injury, spinal cord injury, atherosclerosis-related infarctions, arthritis, and muscular dystrophy. Optionally, any of the banks of ADSC above can comprise carboxymethylcellulose (CMC).

In another aspect, the invention provides for a composition comprising a purified population of non-human ADSCs and CMC for use in transplantation. In one aspect, the transplantation is xenotransplantation where the xenotransplantation does not result in any significant rejection of the composition.

BRIEF DESCRIPTION OF THE DRAWINGS

FIG. 25 shows results of experiments on the effect of FGFR inhibitor on endothelial differentiation. RADSC-1 cells were grown in EGM2 or EBM2 supplemented with FGF2 and vitamin C in the presence or absence of FGFR inhibitor PD173074. The cells were then assayed for LDL-uptake. If viewed in color, then the red indicates the presence of LDL, which was in a conjugated form with the red fluorescence dye DiI. RADSC-1 cells were also grown in VEGF/vitamin C-supplemented EBM2 for the purpose of excluding the involvement of VEGF signaling, as PD173074 is known to have a weak inhibitory effect on VEGF receptor. Experiments were repeated 3 times.

DETAILED DESCRIPTION

Figure 1:
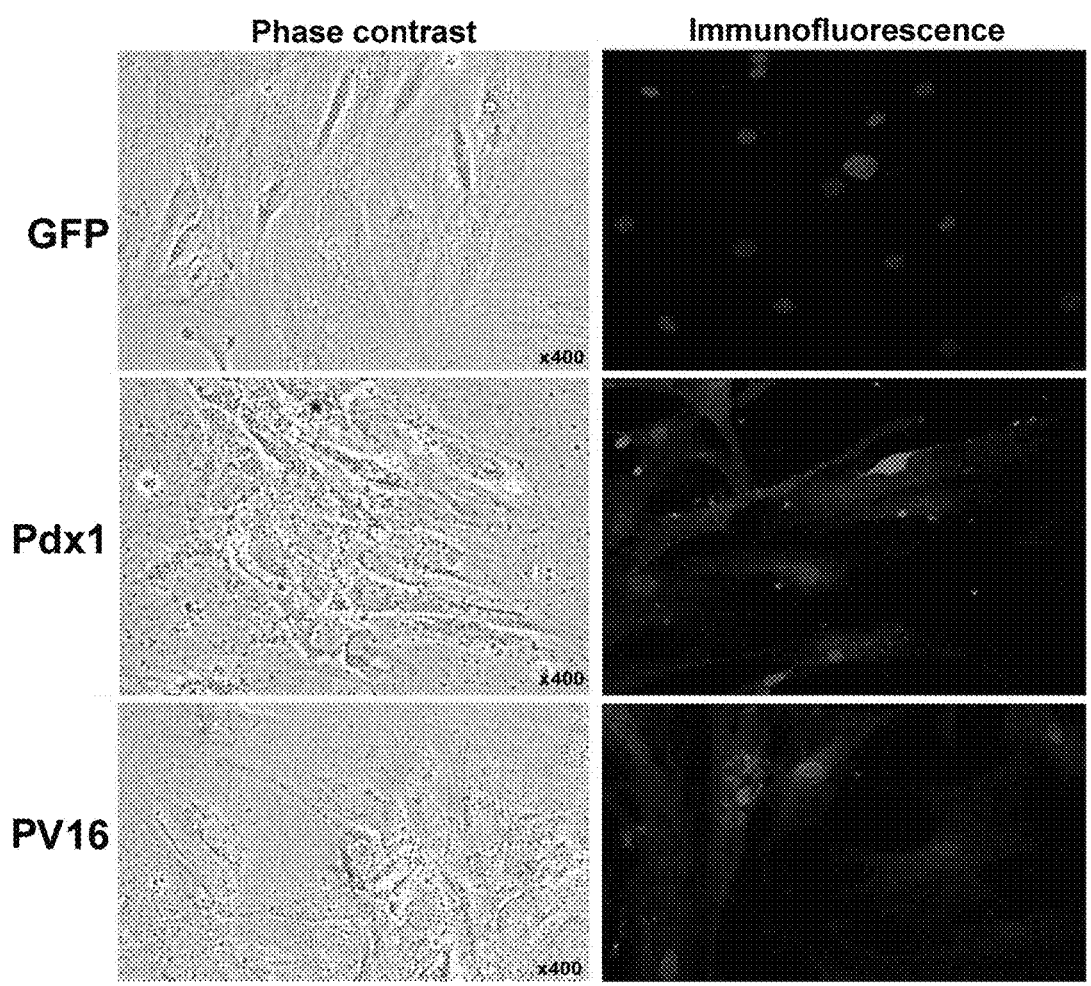
FIG. 1 depicts the results of experiments on generation of insulin-producing cells. Human ADSC were transduced with GFP (control), Pdx1 or Pdx1-PV-16 (PV-16). Phase contrast microscopy showed that the Pdx1- and PV-16-transduced cells had insulin-like granules in the cytoplasm and culture media. Immunofluorescence microscopy showed that the Pdx1- and PV-16-transduced cells stained positive for insulin. Nuclear staining with DAPI was used to locate cells.

The invention provides for compositions and methods for treating non-human mammals for various conditions and alleviating the discomfort and/or pain associated with various conditions in the non-human mammals.

Unless defined otherwise, all technical and scientific terms used herein have the same meaning as is commonly understood by one of ordinary skill in the art to which this invention belongs.

If a definition set forth in this section is contrary to or otherwise inconsistent with a definition set forth in patents, published patent applications and other publications that are herein incorporated by reference, the definition set forth in this section prevails over the definition that is incorporated herein by reference.

I. General Techniques

The practice of the present invention will employ, unless otherwise indicated, conventional techniques of stem cell biology, cell culturing, molecular biology (including recombinant techniques), microbiology, cell biology, biochemistry and immunology, which are within the skill of the art. Such techniques are explained fully in the literature, such as, *Molecular Cloning: A Laboratory Manual*, third edition (Sambrook et al., 2001) Cold Spring Harbor Press; *Oligonucleotide Synthesis* (P. Herdewijn, ed., 2004); Animal Cell Culture (R. I. Freshney), ed., 1987); *Methods in Enzymology* (Academic Press, Inc.); *Handbook of Experimental Immunology* (D. M. Weir &C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991) *Short Protocols in Molecular Biology* (Wiley and Sons, 1999), *Embryonic Stem Cells: A Practical Approach* (Notaranni et al. eds., Oxford University Press 2006); *Essentials of Stem Cell Biology* (R. Lanza, ed., Elsevier Academic Press 2006); *Stem Cell Assays (Methods in Molecular Biology)* (Mohan C. Vemuri, Ed., Humana Press; first edition (Aug. 10, 2007); *Mesenchymal Stem Cells: Methods and Protocols (Methods in Molecular Biology)* (Darwin J. Prockop, Donald G. Phinney, Bruce A. Bunnell, Eds., first edition (Mar. 7, 2008)); *Handbook of Stem Cells* (Robert Lanza, et al., Eds., Academic Press (Sep. 14, 2004); *Stem Cell Culture* Vol 86: *Methods in Cell Biology* (Jennie P. Mather, Ed., Academic Press, first edition (May 15, 2008)); *Practical Hematopoietic Stem Cell Transplantation* (Andrew J. Cant, et al. Eds., Wiley-Blackwell, first edition (Jan. 22, 2007)); *Hematopoietic Stem Cell Protocols* (Kevin D. Bunting, Ed., Humana Press, 2nd ed. edition (Jan. 31, 2008)); *Bone Marrow and Stem Cell Transplantation (Methods in Molecular Medicine)* (Meral Beksac, Ed., Humana Press; first edition (May 3, 2007)); *Stem Cell Therapy and Tissue Engineering for Cardiovascular Repair: From Basic Research to Clinical Applications* (Nabil Dib, et al., Eds., Springer, first edition (Nov. 16, 2005)); *Blood And Marrow Stem Cell Transplantation: Principles, Practice, And Nursing Insights* (Kim Schmit-Pokorny (Author) and Susan Ezzone (Editor), Jones & Bartlett Publishers; third edition (May 22, 2006)); *Hematopoietic Stem Cell Protocols* (Christopher A. Klug and Craig T. Jordan, Eds., Humana Press; first edition (Dec. 15, 2001)); and *Clinical Bone Marrow and Blood Stem Cell Transplantation* (Kerry Atkinson, et al., Eds., Cambridge University Press; third edition (Dec. 8, 2003)).

II. Definitions

"Adipose-derived stem cells," "adipose tissue-derived stem cells," and ADSC (or ADSCs) are used interchangeably herein and refers to multipotent stromal cells or stem cells that originate from adipose tissue and are capable of self-renewal. "Adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may comprise a primary cell culture or an immortalized cell line. The adipose tissue may be from any non-human mammal having fat tissue. Adipose tissue can be derived from the non-human mammal to be treated (i.e., autologous tissue) or a clone of the subject or from a different species (i.e., xenogeneic) or from the same species of non-human mammal but not the non-human mammal to be treated (i.e., allogeneic). These cells express a unique combination of cell surface proteins that can include, but are not limited to, stem cell marker CD 34 and CD 90, the tetraspan protein CD9, CALLA (CD10), aminopeptidase N (CD13), integrin 1 (CD29), hyaluronate receptor (CD44), integrin .alpha. 4 and 5 (CD49d, CD49e), ICAM-1 (CD54), decay accelerating factor (CD55), complement protectin (CD59), endoglin (CD105), VCAM-1 (CD106), Muc-1,8 (CD146), and ALCAM (CD166) (Gronthos, et al. *J. Cell Physiol.* (2001) October; 189(1):54 63). In one aspect, ADSCs derived from porcine species are generally positive for CD90, CD44, CD29 and generally negative for CD31, CD45 and CD11. See, e.g., Valina et al., *European Heart Journal* 28:2667-77 (2007) which discloses that cultured pig ADSCs are positive for CD90 (97.3+ 0.62%), CD44 (98.27+0.38%), and CD29 (98.2+0.87%) and negative for CD31 (0.03+0.05%), CD45 (0.45+0.41%), and CD11 (0.17+0.17%).

As used herein, the term "preparation" or "purified preparation" of multipotent or pluripotent ADSCs refers to a preparation of one or more cells that has been manipulated to provide a preparation of cells that is substantially free of additional components. In some aspects, the cell preparation is at least about 60%, by weight or number, free from other components that are present when the cell is produced. In various aspects, the cell is at least about 65%, at least about 70%, at least about 75%, at least about 80%, at least about 85%, at least about 90%, 91%, 92%, 93%, 94%, 95%, 96%, 97%, 98% or at least about 99%, by weight or number, pure. A purified cell preparation can be obtained, for example, by purification (e.g., extraction) from a natural source, fluorescence-activated cell-sorting, or other techniques known to the skilled artisan. Purity can be assayed by any appropriate method, such as fluorescence-activated cell-sorting (FACS) or by visual examination.

"Purity" as used to describe the purity of stem cells does not refer to the presence of only stem cells in the composition but rather indicates that the stem cells have been manipulated such that they have been removed from their natural tissue environment and indicates their relationship to the other cells present in the resulting population.

As used herein, the term "multipotent" or "pluripotent" refers to an ADSC's potential to differentiate into cells of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Pluripotent or multipotent stem cells can give rise to any fetal or adult cell type. Alone they cannot develop into a fetal or adult animal because they lack the potential to contribute to extraembryonic tissue (e.g., placenta in vivo or trophoblast in vitro).

"Non-human mammals" include, but are not limited to, farm animals, sport animals, pets, non-human primates, mice and rats. Farm animals can include, but are not limited to, pigs, cows, horses, goats, and sheep. Pets include, but are not limited to, dogs, cats, rabbits, and ferrets. Other animals within the scope of this definition include, but are not limited to, monkey, baboon, chimpanzee, orangutan, tiger, lion, bear, cheetah, and llama. A non-human mammal can also be referred to as "subject" herein.

By "treatment" or "treating" is meant an approach for obtaining a beneficial or desired result, including clinical results (which include veterinary clinic or hospital). For purposes of this invention, beneficial or desired results include, but are not limited to, alleviation of symptoms associated with a condition diminishment of the extent of the symptoms associated with a condition, prevention of a worsening of the symptoms associated with a condition, or delaying the development of a disease or condition. In some aspects, treatment with a one or more cells disclosed herein is accompanied by no or fewer side effects than are associated with currently available therapies.

"Receiving treatment" includes initial treatment and/or continuing treatment. As used herein, "treatment" is an approach for obtaining beneficial or desired results, preferably including clinical results from treatment in a veterinary clinic or hospital. For purposes of this invention, beneficial or desired clinical results include, but are not limited to, the stabilization or improvement of the health-related quality of life of a non-human mammal suffering from various medical conditions.

As used herein, "delaying" development of a disease or condition means to defer, hinder, slow, retard, stabilize and/or postpone development of the disease or condition. This delay can be of varying lengths of time, depending on the history of the disease and/or subject being treated. As is evident to one skilled in the art, a sufficient or significant delay can, in effect, encompass prevention, in that the subject does not develop the disease or condition. For example, the method may reduce the probability of disease development in a given time frame and/or reduce the extent of the disease in a given time frame, when compared to not using the method. In some aspects, such comparisons are based on clinical studies using a statistically significant number of subjects. Disease development can be detectable using standard clinical techniques. Development may also refer to disease progression that can be initially undetectable and includes occurrence, recurrence, and onset.

"Palliating" pain (e.g., pain associated with an inflammatory disease such as a type of arthritis) or one or more symptoms of a pain means lessening the extent of one or more undesirable clinical manifestations of pain in non-human mammal treated with a composition of ADSC in accordance with the invention.

An "effective amount" (when used in the treatment or prophylaxis context, or in the context of palliating pain or alleviating the symptoms of a particular condition) is an amount sufficient to effect beneficial or desired results including clinical results. An effective amount can be administered in one or more administrations. For purposes of this invention, an effective amount of ADSC is a certain amount of cells that can reduce one of more symptoms of the conditions for which the non-human mammal is being treated. For example, reduction of limping in a non-human mammal to whom ADSC has been administered is one symptom for arthritis in a non-human animal and observation of this reduction of this particular symptom could mean that an effective amount of ADSC was given to the non-human mammal. In one aspect, the ADSC are cultured further to induce them to differentiate down a particular pathway. In another aspect, the ADSC are cultured in a manner where no differentiation occurs.

As used herein, "in need thereof" includes non-human mammals who have a condition or disease or are "at risk" for the condition or disease. As used herein, an "at risk" non-human mammal is a non-human mammal who is at risk of development of a condition. A non-human mammal "at risk" may or may not have a detectable disease or condition, and may or may not have displayed detectable disease prior to the treatment methods described herein. "At risk" denotes that a non-human mammal has one or more so-called risk factors, which are measurable parameters that correlate with development of a disease or condition and are known in the art. A non-human mammal having one or more of these risk factors has a higher probability of developing the disease or condition than a subject without these risk factor(s). These risk factors include, but are not limited to, age, sex, diet, history of previous disease, presence of precursor disease, genetic (i.e., hereditary) considerations, breeding protocols and considerations, and environmental exposure.

By "pharmaceutically acceptable carrier" is meant any material which, when combined with an active ingredient, allows the ingredient to retain biological activity and does not provoke an unacceptable immune response (e.g., a severe allergy or anaphylactic shock) based on the knowledge of a skilled practitioner. Examples include, but are not limited to, any of the standard pharmaceutical carriers such as carboxymethylcellulose (CMC), phosphate buffered saline solutions, water, emulsions such as oil/water emulsion, and various types of wetting agents. Exemplary diluents for aerosol or parenteral administration are phosphate buffered saline or normal (0.9%) saline. An exemplary carrier for the infusion of cells is CMC. Compositions comprising such carriers are formulated by well known conventional methods (see, for example, *Remington's Pharmaceutical Sciences,* 18th edition, A. Gennaro, ed., Mack Publishing Co., Easton, Pa., 1990; and *Remington, The Science and Practice of Pharmacy* 20th Ed. Mack Publishing, 2000, which are each hereby incorporated by reference in their entireties, particularly with respect to formulations).

General reference to "the composition" or "compositions" includes and is applicable to compositions of the invention. The invention also provides pharmaceutical compositions comprising the components described herein.

As used herein, the singular form "a", "an", and "the" includes plural references unless indicated otherwise. For example, "an" ADSC includes one or more adipose tissue-derived stem cells.

Reference to "about" a value or parameter herein includes (and describes) aspects that are directed to that value or parameter per se. For example, description referring to "about X" includes description of "X."

It is understood that aspects and aspects of the invention described herein include "comprising," "consisting," and "consisting essentially of" aspects and aspects.

III. Adipose-Derived Stem Cells (ADSC) and Their Isolation

Adipose tissue offers a source of multipotent stromal cells. Adipose tissue is readily accessible and abundant in many subjects (e.g., non-human mammals). It is well documented that adipocytes are a replenishable cell population. Even after surgical removal by liposuction or other procedures, it is common to see a recurrence of adipocytes in a subject over time. This suggests that adipose tissue contains stromal stem cells that are capable of self-renewal.

Methods for the ordinary isolation, expansion, and differentiation of human adipose tissue-derived stem cells have been described previously (Zuk et al., *Tissue Engineering* (2001) 7:211-228; Burris et al *Mol Endocrinol* 1999, 13:410 7; Erickson et al Biochemical & Biophysical Research Communications 2002, 290:763 9; Gronthos, et al. *J Cell Physiol.* 2001 October; 189(1):54 63; Halvorsen, et al, *Metabolism* 2001, 50:407 413; Halvorsen, et al, *Tissue Eng.* 2001 December; 7(6):729 41; Harp, et al. *Biochem Biophys Res Commun* 2001, 281:907 912; Saladin et al 1999, *Cell Growth & Diff* 10:43 48; Sen, et al. *Journal of Cellular Biochemistry* 2001, 81:312 319; Zhou et al *Biotechnol Techniq* 1999, 13:513 517). Adipose tissue-derived stem cells are obtained from minced human adipose tissue by collagenase digestion and differential centrifugation according to known techniques (Halvorsen, et al, *Metabolism* 2001, 50:407 413; Hauner, et al, *J Clin Invest* 1989, 84:1663 1670; Rodbell, et al, *J Biol Chem* 1966, 241:130 139). These techniques are equally applicable to the isolation, expansion, and differentiation of non-human mammal adipose tissue-derived stem cells. See, e.g., Fotuhi P., et al., *Europace,* 9(12):1218-21 (2007); Madonna R., et al., *Stem Cell,* 26(1): 202-11 (2008); Huang T., et al., *J Spinal Cord Med.,* 30 Suppl. 1:S35-40 (2007); Hemmrich K., et al., *J Surg Res.,*

144(1):82-8 (2008); Qu C Q, et al., *In Vitro Cell Dev Biol Anim.*, 43(2):95-100 (2007); Wang K. H., et al., *Biotechnol. Appl. Biochem.* (2008); Williams K. J., *Cells Tissues Organs*, (2008); and Valina C, et al., *Eur Heart* 1, 28(21): 2667-77 (2007).

ADSC may be isolated from various non-human mammals, including but not limited to porcine, bovine, canine, equine and feline species. In one aspect, a subject from whom ADSC can be isolated and used for therapeutic and/or prophylactic purposes is a porcine species. Porcine species are commonly raised for purpose of providing parts for xenotransplantation (e.g., valve for human heart). Accordingly, porcine ADSC may be used for xenotransplantation into other non-human animals. In another aspect, the invention provides for ADSC obtained from privately owned pets, whose procurement may be regulated by the Food and Drug Administration (FDA). The ADSC from these pets may be used for xenotransplantation, allogeneic transplantation or syngeneic transplantation.

In one aspect, the invention provides for ADSC that are xenogeneic to the recipient of the ADSC-based treatment. Non-limiting examples of types of ADSC that can be used are bovine, equine, ovine and porcine. In another aspect, the invention provides for ADSC that are allogeneic to the recipient of the ADSC-based treatment. In another aspect, the invention provides for ADSC that are syngeneic to the recipient of the ADSC-based treatment. In another aspect, the invention provides for ADSC that are autologous to the recipient of the ADSC-based treatment.

ADSC from non-human mammals may be isolated in any way known to one of skill in the art. In one aspect of the present invention, ADSCs may be isolated according to the following non-limiting method. First, isolated adipose tissue (i.e., fat tissue or liposuction fat) is rinsed with PBS containing 1% penicillin and streptomycin, minced into small pieces, then mixed with a solution containing 0.075% collagenase Type IA (Sigma-Aldrich, St. Louis, Mo.) at 5:1 v/v ratio of collagenase solution:adipose. After incubation for 1 hour at 37° C. with vigorous shaking, the product is then centrifuged at 220×g for 10 minutes at room temperature. Three layers are formed: the upper lipid layer, the middle collagenase layer and the bottom cellular pellet. The middle layer is collected and filtered through a 200 μm filter followed by centrifugation. The recycled collagenase Type IA, in the flow-thru, is used in a second round to digest the fresh adipose tissue again, using a higher ratio (7:1, by volume) than the first round. The bottom cellular pellet contains the stem cells.

ADSCs or adipose tissue comprising ADSCs can be preserved or stored prior to further purification, differentiation, administration to a subject, or any other use. Although it has been reported that the adipose tissue could be stored at room temperature for 24 hours and at 4° C. for 1-3 days, the viable cells in the adipose tissue declined dramatically in storage. Thus, in one aspect, the invention provides for methods for preserving the viability of ADSCs or adipose tissue which utilizes an adipose tissue preservation solution (ATPS), wherein the ATPS contains as its essential ingredient the enzyme superoxide dismutase (SOD). In one aspect, the superoxide dismutase is isolated from mammalian erythrocytes. One of skill in the art may readily procure SOD from commercially available sources, such as Sigma-Aldrich (which also sells SOD isolated from bovine RBC or liver.

In one non-limiting aspect, the ATPS consists of 200 mg/ml $KH_2PO_4$, 200 mg/L KCl, 2.16 g/L Na2HPO4.7H2O, 8 g/L NaCl, 30,000 units/L SOD, and 5 g/L bovine serum albumin (BSA). To preserve non-human mammal adipose-derived stem cells, $1\times10^6$ adipose derived stem cells may be mixed with 1 ml of ATPS and stored at 4° C. One skilled in the art will recognize that the concentrations of reagents comprised by the ATPS may be altered to modest degrees without substantially affecting the desirable properties of the ATPS.

It is well known that the stromal vascular fraction derived from adipose tissue digestion consists of many type of cells, such as stem cells, endothelium, smooth muscle cell, and other terminally differentiated cells. "Panning," an immunoselection method used to enrich a specific cell population from a diverse mixture of cell types, has been described in various cell culturing textbooks and in references known to one of the skill in the art. This method is based on the selective capabilities of antibodies bound to cell culture dishes. A mixture of cell types is cultured on the antibody-coated plates and allowed to bind for a short period of time. The non-adherent cells (those that do not bind antibody) can then be gently eluted from the culture dish allowing bound cells to be harvested. This method facilitated the development of other new technologies such as density-gradient separations and methods that exploit unique surface binding properties of specific cell types. For example, the development of magnetic bead technology allowed repetitive washing of bead-bound cells, greatly improving the potential purity of separations. The size and composition of the paramagnetic beads utilized by various companies varies significantly and further refinements/improvements have been regularly forthcoming.

Accordingly, in one aspect of the present invention, adipose-derived stem cells are selected using a combination of antibodies that, together, can be used to detect the presence of the CD34, CD90 and SSEA1 cell markers. Other antibodies can be used in addition to these markers, e.g., those markers disclosed in the published U.S. Pat. App. No. 2006/0147430 to Sayre et al. Following identification of positive cells, the cells can be cultured, studied further, or administered to subjects in one or more of the methods of treatment disclosed herein.

IV. Compositions

The invention also provides for therapeutic compositions which are useful in practicing the therapeutic methods of this invention. In some embodiments, the ADSCs used are xenogeneic to the recipient. The invention also provides for a bank of ADSC which can be used as a "universal donor" for treatment (therapeutic or prophylactic) for a variety of non-human mammals, thus reducing the likelihood of transplant rejection.

In one aspect of the invention, a therapeutic composition includes, in admixture, a pharmaceutically acceptable excipient (carrier) or media and the ADSC of the present invention, including cells or tissues derived therefrom, alone or in combination with one or more bioactive agents, and at a strength effective for administration by various means to a subject experiencing cellular or tissue loss or deficiency.

In another aspect, the present invention provides for therapeutic compositions for use in methods which comprise or are based upon the ADSC of the present invention, including lineage-uncommitted populations of cells, lineage-committed populations of cells or tissues derived therefrom, along with a pharmaceutically acceptable carrier or media. It is to be understood that the invention also encompasses therapeutic compositions comprising bioactive agents that act on or modulate the ADSC of the present invention and/or the cells or tissues derived therefrom, along with a pharmaceutically acceptable carrier or media.

The preparation of cellular or tissue-based therapeutic compositions is well understood in the art. Such compositions may be formulated in a pharmaceutically acceptable media. The cells may be in solution or embedded in a matrix. The preparation of therapeutic compositions with bioactive agents (such as, for example, growth factors) as active ingredients is well understood in the art. The active therapeutic ingredient is often mixed with excipients or media which are pharmaceutically acceptable and compatible with the active ingredient. In addition, if desired, the composition can contain minor amounts of auxiliary substances such as wetting or emulsifying agents, pH buffering agents which enhance the effectiveness of the active ingredient.

A bioactive agent can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of ADSCs

The therapeutic compositions of the present invention are administered in a manner compatible with the dosage formulation, and in a therapeutically effective amount. The quantity to be administered depends, for instance, on the subject and debilitation to be treated. However, suitable dosages of the therapeutic composition of the present invention may range from about $0.05-100.0 \times 10^6$ adipose-derived stem cells/10 mm of treatment site, preferably about $0.10-50.0 \times 10^6$ adipose-derived stem cells/10 mm of treatment site, and more preferably about $0.5-5.0 \times 10^6$ adipose-derived stem cells/10 mm of treatment site. Suitable regimens for initial administration and follow on administration are also variable, but can include an initial administration followed by repeated doses at one or more intervals as desired or indicated (e.g. weeks, months, or years) by a subsequent injection or other administration.

One of skill in the art may readily determine the appropriate concentration of cells for a particular purpose. An exemplary dose is in the range of about $0.05-100.0 \times 10^6$ cells per treatment site per day. In a non-limiting example, approximately $5 \times 10^6$ ADSCs are injected into a non-human's joint (e.g., a stiff joint) to treat osteoarthritis. Precise administration schedules for the therapeutic composition depend on the judgment of the veterinarian and the desired result and are therefore peculiar, to a certain extent, to each subject.

The ADSCs or differentiated cells of the present invention can be administered by injection into a target site of a subject, preferably via a delivery device, such as a tube, e.g., catheter. In one aspect, the tube additionally contains a needle, e.g., a syringe, through which the cells can be introduced into the subject at a desired location. Specific, non-limiting examples of administering cells to subjects may also include administration by subcutaneous injection, intramuscular injection, intraarticular, or intravenous injection. If administration is intravenous, an injectable liquid suspension of cells can be prepared and administered by a continuous drip or as a bolus. In another aspect, if the medical condition to be treated is dilated cardiomyopathy, then one of skill in the art (e.g., a veterinarian) can deliver ADSCs using catheter-based injection into the coronary artery or in a manner such that the ADSCs are trapped in capillary beds so that they can be distributed to surrounding tissue.

Cells may also be inserted into a delivery device, e.g., a syringe, in different forms. For example, the cells can be suspended in a solution contained in such a delivery device. As used herein, the term "solution" includes a pharmaceutically acceptable carrier or diluent in which the cells of the invention remain viable. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating ADSC or differentiated cells as described herein, in a pharmaceutically acceptable carrier or diluent and, as required, other ingredients enumerated above, followed by filter sterilization.

The cells may be administered systemically (for example intravenously) or locally (for example directly into a myocardial defect under echocardiogram guidance, or by direct application under visualization during surgery). For such injections, the cells may be in an injectable liquid suspension preparation or in a biocompatible medium which is injectable in liquid form and becomes semi-solid at the site of damaged tissue. A conventional intra-cardiac syringe or a controllable endoscopic delivery device can be used so long as the needle lumen or bore is of sufficient diameter (e.g., 30 gauge or larger) that shear forces will not damage the cells being delivered.

Cells may be administered in any manner that permits them to graft to the intended tissue site and reconstitute or regenerate the functionally deficient area. Support matrices into which the ADSC can be incorporated or embedded include matrices which are biocompatible, recipient-compatible and which degrade into products which are not harmful to the recipient. These matrices provide support and protection for ADSC and differentiated cells in vivo.

Natural and/or synthetic biodegradable matrices are examples of such matrices. Natural biodegradable matrices include plasma clots, e.g., derived from a mammal, collagen, fibronectin, and laminin matrices. Suitable synthetic material for a cell transplantation matrix must be biocompatible to preclude migration and immunological complications; and should be able to support extensive cell growth and differentiated cell function. It must also be resorbable, allowing for a completely natural tissue replacement. The matrix should be configurable into a variety of shapes and should have sufficient strength to prevent collapse upon implantation. A variety of studies indicate that the biodegradable polyester polymers made of polyglycolic acid fulfill all of these criteria, as described by Vacanti et al., *J. Ped. Surg.*, 23:3-9 (1988); Cima, et al., *Biotechnol. Bioeng.* 38:145 (1991); Vacanti, et al., *Plast. Reconstr. Surg.*, 88:753-9 (1991). Other synthetic biodegradable support matrices include synthetic polymers such as polyanhydrides, polyorthoesters, and polylactic acid. Further examples of synthetic polymers and methods of incorporating or embedding cells into these matrices are also known in the art. See, e.g., U.S. Pat. Nos. 4,298,002 and 5,308,701.

Attachment of the cells to the polymer may be enhanced by coating the polymers with compounds such as basement membrane components, agar, agarose, gelatin, gum arabic, collagens types I, II, III, IV and V, fibronectin, laminin, glycosaminoglycans, mixtures thereof, and other materials known to those skilled in the art of cell culture. All polymers for use in the matrix must meet the mechanical and biochemical parameters necessary to provide adequate support for the cells with subsequent growth and proliferation.

One of the advantages of a biodegradable polymeric matrix is that angiogenic and other bioactive compounds can be incorporated directly into the support matrix so that they are slowly released as the support matrix degrades in vivo. As the cell-polymer structure is vascularized and the structure degrades, ADSC may differentiate according to their inherent characteristics. Factors, including nutrients, growth factors, inducers of differentiation or de-differentiation (i.e., causing differentiated cells to lose characteristics of differentiation and acquire characteristics such as proliferation and more general function), products of secretion, immunomodulators, inhibitors of inflammation, regression factors, bioactive agents which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., vascular growth factors such as vascular endothelial growth factor (VEGF), epidermal growth factor (EGF), and heparin binding epidermal growth factor like growth factor (HB-EGF), could be incorporated into the matrix or provided in conjunction with the matrix. Similarly, polymers containing peptides such as the attachment peptide RGD (Arg-Gly-Asp) can be synthesized for use in forming matrices (see, e.g., U.S. Pat. Nos. 4,988,621, 4,792,525, 5,965,997, 4,879,237 and 4,789,734).

In another example, the cells may be transplanted in a gel matrix (such as Gelfoam from Upjohn Company) which polymerizes to form a substrate in which ADSC or differentiated cells can grow. A variety of encapsulation technologies have been developed (e.g. Lacy et al., *Science* 254: 1782-84 (1991); Sullivan et al., Science 252:718-712 (1991); WO 91/10470; WO 91/10425; U.S. Pat. Nos. 5,837, 234; 5,011,472; 4,892,538).

PLGA or poly(lactic-co-glycolic acid) is a Food and Drug Administration (FDA)-approved copolymer which is used in a host of therapeutic devices, owing to its biodegradability and biocompatibility. PLGA is synthesized by means of random ring-opening co-polymerization of two different monomers, the cyclic dimers (1,4-dioxane-2,5-diones) of glycolic acid and lactic acid. Common catalysts used in the preparation of this polymer include tin(II) 2-ethylhexanoate, tin(II) alkoxides, or aluminum isopropoxide. During polymerization, successive monomeric units (of glycolic or lactic acid) are linked together in PLGA by ester linkages, thus yielding alinear, aliphatic polyester as a product. PLGA has been successfully used as a biodegradable polymer because it undergoes hydrolysis in the body to produce the original monomers, lactic acid and glycolic acid. These two monomers are by-products of various metabolic pathways in the body. Since the body is able to effectively break down the two monomers, there is no systemic toxicity associated with using PLGA for drug delivery or biomaterial applications. ADSC mixed with PLGA/carboxymethylcellulose (CMC) have a greater tendency to remain at the injected area compared to ADSC mixed with saline.

V. Genetically Modified Cells

In addition, ADSC can be engineered to contain genes that express growth factors, hormones, and cytokines. For example, the ADSC could be engineered to express beneficial genes, such as, without limitation, VEGF, BDNF, IGF, TGF, NGF and other neurotrophic and vasculotrophic growth factors. Injection of a specifically engineered ADSC may help the regeneration of certain tissues; for example, BDNF for nerves. ADSC can also be engineered to express beta cell-specific gene Pdx-1, which enable ADSC to secrete insulin. Such cells can be transplanted into subjects so as to treat their diabetes mellitus. In another aspect, ADSC may be engineered to produce dystrophin and then implanted into subjects to treat muscular dystrophy. In yet another aspect, ADSC expressing at least one genotypic or phenotypic characteristic of a chondrocyte is genetically modified to express exogenous genes or to repress the expression of endogenous genes and implanted into an animal. The invention provides a method of genetically modifying such cells and populations prior to implantation. It is to be understood that ADSC may be able to differentiate further down the lineage towards organ-specific cells (e.g., chondrocytes) without the aid of genetic modification.

A nucleic acid construct comprising a promoter and the sequence of interest can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication without an origin of replication, the expression of the gene can occur through the transient expression of the introduced-sequence. Alternatively, permanent expression can occur through the integration of the introduced DNA sequence into the host chromosome.

In one aspect, a vector is employed which is capable of integrating the desired gene sequences into the host cell chromosome. Cells which have stably integrated the introduced DNA into their chromosomes can be selected by also introducing one or more markers which allow for selection of host cells which contain the desired nucleic acid sequence. The marker, if desired, can provide for prototrophy to an auxotrophic host, biocide resistance, e.g., resistance to antibiotics, or heavy metals, such as copper, or the like. The selectable marker gene sequence can either be directly linked to the DNA gene sequences to be expressed, or introduced into the same cell by co-transfection. Preferably, expression of the marker can be quantified.

In a preferred aspect, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: 1) the ease with which recipient cells that contain the vector can be recognized and selected from those recipient cells which do not contain the vector; 2) the number of copies of the vector which are desired in a particular host; and 3) whether it is desirable to be able to "shuttle" the vector between host cells of different species.

Preferred eukaryotic vectors include for example, vaccinia virus, SV40, retroviruses, adenoviruses, adeno-associated viruses, lentiviruses and a variety of commercially available, plasmid-based mammalian expression vectors that are familiar to those experienced in the art.

Once the vector or nucleic acid molecule containing the construct(s) has been prepared for expression, the DNA construct(s) can be introduced into an appropriate host cell by any of a variety of suitable means, i.e., transformation, transfection, viral infection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of the heterologous protein.

Introduced DNA being "maintained" in cells should be understood as the introduced DNA continuing to be present in essentially all of the cells in question as they continue to grow and proliferate. That is, the introduced DNA is not diluted out of the majority of the cells over multiple rounds of cell division. Rather, it replicates during cell proliferation and at least one copy of the introduced DNA remains in almost every daughter cell. Introduced DNA may be maintained in cells in either of two fashions. First, it may integrate directly into the cell's genome. This occurs at a rather low frequency. Second, it may exist as an extrachromosomal element, or episome. In order for an episome not to be diluted out during cell proliferation, a selectable marker gene can be included in the introduced DNA and the cells grown under conditions where expression of the marker gene is required. Even in the case where the introduced DNA has integrated in the genome, a selectable marker gene may be included to prevent excision of the DNA from the chromosome.

The genetically modified cells can transiently express the gene of interest or constitutively express the gene of interest. The expression can be either intracellular or on the cell surface. In one aspect of the invention, ADSCs of the invention are genetically modified to transiently express one or more cytokines which are beneficial for treatment of a particular medical condition or to palliate pain. For example, ADSC which have been genetically modified to express anti-inflammatory cytokines (e.g., IL-2) can be transplanted into a location where inflammation is occurring (e.g., arthritic joint). The transplantation then provides a dual benefit to the subject because the ADSC can become a chondrocyte in addition to expressing beneficial, anti-inflammatory cytokines. The transient expression can extend for a period of minutes, hours, days or even weeks. In some embodiments of the invention, the transient expression of the beneficial cytokine is 1, 2, or 3 weeks. In other embodiments of the invention, the transient expression of the beneficial cytokine is the length of time necessary for the symptoms to decrease or even disappear. The decrease or disappearance of symptoms can be determined by one of skill in the art (e.g., a veterinarian) who is treating the subject.

The genetically altered cells can then be introduced into the subject by a variety of methods under conditions for the transgene to be expressed in vivo. As a non-limiting example, the transgene can encode for the production of an extracellular matrix protein, preferably wherein the transgene encodes for the production of collagen. The cells containing the transgene for the extracellular matrix protein can then be introduced into the animal. Alternatively, the cells containing the transgene are injected intraperitoneally or into some other suitable organ depot site.

VI. ADSC Banks

The invention also provides for storage banks of ADSC which have been derived from various species from non-human mammals. Non-limiting examples of types of ADSC that can be used are bovine, equine, ovine and porcine. The ADSC banks allow for deposit and/or storage of ADSC which have been isolated from various from non-human mammals. The ADSC banks allow one of skill in the art (e.g., veterinarian) to treat the animals with ease and with speed. The ADSC banks also allow one of skill in the art to treat the animals with autologous, allogeneic, xenogeneic or syngeneic ADSC as he/she determines to be appropriate. In one aspect, a bank of porcine-derived ADSC which would pass FDA regulation for transplantation (including xenotransplantation) is provided for use in veterinary treatments, both therapeutic as well as prophylactic. In another aspect, a bank of porcine-derived ADSC derived from non-FDA approved sources is provided for use in veterinary treatments, both therapeutic as well as prophylactic. In another aspect, the bank of ADSC is xenogeneic to the recipient of the treatment. In another aspect, the bank of ADSC serves as a universal donor to the recipients of veterinary treatments.

VII. Kits with ADSC Derived from Non-Human Mammals

Also provided are articles of manufacture and kits that include a composition of ADSC derived from any of non-human mammal and suitable packaging. In one aspect, the composition comprises 100% (referring to purity) ADSC. "Purity" does not refer to the presence of only stem cells in the composition but rather indicates that the stem cells have been manipulated such that they have been removed from their natural tissue environment. On other aspects, the composition comprises ADSC of 99.9%, 99.5%, 99%, 98%, 97%, 96%, 95%, 94%, 93%, 92%, 91% or 90% purity. In other aspects, the composition comprises ADSC of 85%, 80%, 75%, or 70% purity. Kits comprising ADSC from non-human mammals are useful for storage and/or shipment. In some aspects, the invention includes a kit with (i) one or more multipotent ADSC or transplantable ADSC derived from one or more non-human mammal and (ii) instructions for using the kit to treat a condition in a non-human mammal in need of such treatment. In various aspects, the invention features a kit with (i) one or more multipotent ADSC or transplantable ADSC derived from one or more non-human mammal and (ii) instructions for using the kit for research or drug screening uses. In another aspect, the composition of ADSC is combined with carboxymethylcellulose (CMC).

Suitable packaging for compositions described herein are known in the art, and include, for example, vials (e.g., sealed vials), vessels, ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed. Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use ADSC derived from non-human mammals generally include information as to dosage, dosing schedule, and route of administration for the intended treatment or industrial use. The kit may further comprise a description of selecting an individual suitable or treatment.

The containers may be unit doses, bulk packages (e.g., multi-dose packages) or sub-unit doses. For example, kits may also be provided that contain sufficient dosages of ADSC to provide effective treatment for a subject for an extended period, such as about any of a week, 2 weeks, 3 weeks, 4 weeks, 6 weeks, 8 weeks, 3 months, 4 months, 5 months, 6 months, 7 months, 8 months, 9 months, or more.

Kits may also include multiple unit doses of cells and instructions for use and packaged in quantities sufficient for storage and use in veterinary clinics, for example, animal hospitals, pharmacies in animal hospitals and supply stores for veterinary clinics and/or animal hospitals.

Additionally, the kits may contain compositions comprising ADSC which are xenogeneic, allogeneic, or syngeneic to the recipient of the treatment.

VIII. Methods of Treatment and Administration of ADSCs

ADSCs may be administered to treat a number of mammalian pathologies including, without limitation, urinary incontinence, osteoarthritis, degenerative myelopathy, diabetes, tissue regeneration, wound healing, scarring, soft tissue defect, fecal incontinence, dilated cardiomyopathy, hip dysplasia, avascular necrosis of the femoral head, ligament injury, tendon injury, spinal cord injury, atherosclerosis-related infarctions, arthritis, and muscular dystrophy. Another use for ADSC is to suppress immune reaction in order to prevent graft-versus-host (GVH) disease. The ADSC can be used for regeneration of tissues or for the various factors and/or enzymes that it can secrete or for its effects on surrounding environment upon differentiation.

Adipose-derived stem cells or differentiated cells may be transplanted into the recipient where the cells will proliferate and differentiate to form new cells and tissues thereby providing the physiological processes normally provided by that tissue. The term "transplanted" as used herein refers to transferring cells alone or cells that are embedded in a support matrix. The cells can be autologous, syngeneic, allogeneic, or xenogeneic. As used herein, the term "tissue" refers to an aggregation of similarly specialized cells united in the performance of a particular function. Tissue is intended to encompass all types of biological tissue including both hard and soft tissue. Soft tissue refers to tissues that connect, support, or surround other structures and organs of the body. Soft tissue includes muscles, tendons (bands of fiber that connect muscles to bones), fibrous tissues, fat, blood vessels, nerves, and synovial tissues (tissues around joints). Hard tissue includes connective tissue (e.g., hard forms such as osseous tissue or bone) as well as other muscular or skeletal tissue.

In another aspect of the present invention, the ADSCs are administered with a pharmaceutically acceptable carrier or excipients. The pharmaceutically acceptable excipients described herein, for example, vehicles, adjuvants, carriers or diluents, are well-known to those who are skilled in the art and are readily available to the public. It is preferred that the pharmaceutically acceptable carrier or excipient be one which is chemically inert to the therapeutic composition and one which has no detrimental side effects or toxicity under the conditions of use.

The choice of excipient or carrier will be determined in part by the particular therapeutic composition, as well as by the particular method used to administer the composition. Accordingly, there are a wide variety of suitable formulations of the pharmaceutical composition of the present invention. The formulations described herein are merely exemplary and are in no way limiting.

Often the physiologically acceptable carrier is an aqueous pH buffered solution. Examples of physiologically acceptable carriers include, but are not limited to, saline, solvents, dispersion media, cell culture media, aqueous buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A. ADSC Treatment for Urinary Incontinence

ADSC may be used to treat various non-human mammals for urinary incontinence. Urinary incontinence (UI) is a debilitating and thus far incurable condition. In one aspect, UI is defined as the involuntary leakage of urine and affects approximately 20% of spayed (ovariohysterectomy) female dogs but is seen in less than 1% of intact female dogs and rarely reported in male canines regardless of gonadal status.

Dogs suffering from UI have some common secondary problems, such as bladder infection and urine scalding. Bladder infection is caused by bacteria that migrate up the urethra and enter the bladder through the more lax urethral opening in dogs with UI. Urine scalding of the skin is a consequence of prolonged contact with the leaked urine, which is highly caustic. In female dogs, UI can occur any time from one week after spaying and is associated with severe management problems that often lead to euthanasia of the animal. UI in spayed female dogs is believed to occur as a consequence of neurological, vascular or hormonal change, rather than the mechanical damage of the lower urinary tract sustained during surgery.

Currently, canine UI is principally treated with phenylpropanolanmine (PPA). PPA is an alpha-adrenergic agonist and stimulates the secretion of norepinephrine, a hormonal substance that increases urethral sphincter muscle tone. In 1999, the Federal Food and Drug Administration banned PPA for human use because it increases the risk of hemorrhagic stroke (bleeding in the brain or into tissue surrounding the brain).

Stem cell therapy for UI has been successfully demonstrated in human medicine. Presently, stem cells are isolated from the subjects' skeletal muscles and are injected into the urethral sphincter, resulting in muscle cell regeneration and enhanced urethral contractility. However, due to the scarcity of such stem cells and the limited size of the muscle biopsy, this procedure requires prolonged culturing of the isolated stem cells. In addition, these cells are destined to become muscle cells only and therefore cannot restore other cell types of the urethra (such as nerve and blood vessels). In contrast, ADSC can be obtained in abundance and can differentiate into a wide variety of cell types including neurons, vascular endothelial and smooth muscle cells, thus providing an advantage over other types of therapy.

Accordingly, ADSC can be used to treat UI. In one aspect, the ADSC that is used is characterized as a universal donor. The ADSC acting as the universal donor may be stored at the veterinary clinic or animal's hospital for ease and speed of treatment. The subject being treated for UI has an effective amount of ADSC injected into the sphincter area of the urethra. An effective amount is in the range of 1-10 million cells per animal or 5 million/10 kg, depending on the size of the animal. Precision injection can be accomplished by using an uroscope that enables both visualization and injection. One of skill in the art (e.g., veterinarian) can adjust the volume of the suspension and the number of cells proportionally to the weight of the subject.

After the treatment procedure, the owner of the subject should take care to monitor the subject on a daily basis to observe the following characteristics: monitoring the site of injection for signs of reaction such as redness, pain, and heat, monitoring the animal for signs of anaphylactic reaction and urinary blockage, any other unusual signs in the animal, such as persistent nausea, fatigue, lethargy, decreased appetite and difficult urination. If any of these characteristics are observed, then the owner of the subject should inform the veterinarian immediately so that the veterinarian can take the appropriate actions to bring the subject into a better state of health. A veterinarian's evaluation can be conducted at regular intervals after the treatment, for example, at 10-15, 25-30 and 55-60 days after treatment.

B. ADSC Treatment for Osteoarthritis (OA)

ADSC may be used to treat various non-human mammals for osteoarthritis (OA). OA is the most common cause of chronic pain in dogs, with more than 20%, or 10 to 12 million dogs, afflicted in the United States at any time. OA is characterized by degeneration of the articular cartilage, with loss of matrix, fibrillation, and formation of fissures, and can result in complete loss of the cartilage surface. Chondrocytes, the only cells of articular cartilage, maintain homeostatic synthesis and degradation of the extracellular matrix via the secretion of macromolecular components (collagen, glycosaminoglycans, and hyaluronic acid) and modulation of the extracellular matrix turnover. In OA, there exists an overproduction of destructive and proinflammatory mediators relative to the anabolic and reparative substances, resulting in the progressive destruction of articular cartilage.

Presently, stem cell therapy has been applied in clinical settings to humans, horses and dogs. In horses, high success rates (~70%) have been achieved with the use of adipose tissue-derived stem cells (ADSC) to treat tendon injury, ligament injury, osteoarthritis (OA), and osteochondral defects. In dogs, ADSC treatment for OA appears to be effective as well. Other canine diseases that are potential targets for stem cell therapy include tendon and ligament injuries, hip dysplasia, avascular necrosis of femoral head, dilated cardiomyopathy, spinal cord injury, degenerative myelopathy, urinary incontinence (UI), and muscular dystrophy.

Currently, OA is principally treated with NASID. However, numerous scientific studies and clinical experience suggest that NSAID do not provide complete pain relief. In contrast to drug therapy, cellular therapies such as ADSC therapy do not rely on a single target receptor or pathway for their action. Cellular therapy functions trophically by secreting cytokines and growth factors and by recruiting endogenous cells to the injured site, and it may promote cellular differentiation into the resident lineages. Mesenchymal stem cells, which include ADSC, are known to communicate with cells of their local environment, suppress immunoreactions, and inhibit apoptosis. Recent studies also show that bone marrow stem cells (which have similar regenerative capability as ADSC) can deliver new mitochondria to damaged cells, thereby rescuing aerobic metabolism. Thus, ADSC therapy can reduce pain and enhance healing in OA subjects, resulting in improved quality of life.

Accordingly, ADSC can be used to treat OA. In one aspect, the ADSC that is used is characterized as a universal donor. The ADSC acting as the universal donor may be stored at the veterinary clinic or animal's hospital for ease and speed of treatment. In one aspect, the invention provides treatment of non-human mammals, such as dogs, who are suffering from OA. While OA can afflict virtually any joints, it is most frequently associated with the stifle and hip joints. The treatment may be effectuated by injection of a suspension of ADSC into these joints. It is well within the knowledge of one of skill in the art (e.g., veterinarian) to adjust the volume of the cell suspension and the number of cells proportional to the size of the subject. As a non-limiting example, a 20-kg dog can receive 5 million ADSC in 0.5 ml PBS per joint. Following the treatment, owners are counseled to leash-walk their dogs 30 minutes daily. Any oral medications that the non-human mammal is taking prior to ADSC treatment are allowed to continue. Any intraarticular treatments prior to ADSC treatment should discontinue.

Post-treatment, veterinary evaluation will incorporate history, physical examination, and lameness examination including joint mobility and notation of pain on manipulation. Clinical outcome measures will be based on veterinary orthopedic evaluation using a numerical rating scale based on a standardized questionnaire. Baseline results for both owner and veterinary evaluations can be recorded between 2 and 14 days before the dogs receive either the test or control preparation by intraarticular injection. Follow-up visits to the veterinary clinic can be done at 30, 60, and 90 days after the dog's intraarticular injection. At each visit, owners can be asked to complete a numeric rating scale (1 (best) to 5 (worst)) as part of a standard questionnaire adapted from the Cincinnati Orthopedic Disability Index, which include evaluation of the following parameters: walk, run, jump, turning suddenly, getting up from lying down, lying down from standing, climbing stairs, descending stairs, squatting to urinate or defecate, stiffness in the morning, stiffness in the evening, difficulty walking on slippery floors, and willingness to play voluntarily.

C. ADSC Treatment for Healing Wounds

ADSCs can also be administered to non-human mammals for the purpose of accelerating wound healing and reducing scar formation. This has application both for improved cosmesis (i.e. to improve scar healing purely for cosmetic purposes), and, as an adjunct to improve surgical scars within the body (e.g. excessive scarring at surgical anastomosis sites can lead to surgical complications, such as anastomosis site contractures. Local injection of ADSC at the time of surgery, or, in a delayed fashion, can improve surgical tissue site healing and reduce the incidence of post-surgical complications due to excessive scarring.)

Accordingly, in one aspect of the invention, ADSCs are injected subcutaneously at the desired location, e.g., along the suture site of a surgical wound. In certain aspects, the use of support material such as Matrigel or microspheres with CMC may be introduced to further localize the ADSCs to the site of treatment. The introduction of ADSCs to the wound site leads to the differentiation of the ADSCs in a manner that mimics the body's natural response to a wound. For example, ADSCs appear to spontaneously differentiate into the other cell types that comprise the natural wound healing apparatus, e.g., fibroblasts and inflammatory cells or newly formed blood vessels.

D. Prophylactic Uses for ADSC

ADSC of this invention is also used as a prophylaxis to delay the development of hip dysplasia and avascular necrosis of femoral head by administering an effective amount of ADSC to the hip or femoral head, respectively. An effective amount is in the range of 1-10 million cells per animal or 5 million/10 kg, depending on the size of the animal, which is readily determined by one of skill in the art (e.g., a veterinarian).

EXAMPLES

The examples, which are intended to be purely exemplary of the invention and should therefore not be considered to limit the invention in any way, also describe and detail aspects and aspects of the invention discussed above.

Example 1

Experimental Treatment of Canine Urinary Incontinence with Adipose Tissue-Derived Stem Cells Materials and Methods
Animal Selection Female dogs with demonstrable UI symptoms are selected for this study. These symptoms include dribbling of urine, loss of voluntary control, and/or urine-scald dermatitis. To ensure that the subjects' UI symptoms are resulted from urethral deficiency, they must demonstrate responsiveness to PPA treatment. Each owner also agrees to enter this experimental study by signing a consent form, which indicates that (1) the dog will be subjected to a test injection of ADSC in the hind leg so as to ensure the lack of immune reaction, (2) PPA treatment for the dog will be withdrawn for a few days (up to a week) so as to allow the return of UI symptoms, (3) the dog must demonstrate resumed UI symptoms for at least 3 days before being subjected to ADSC treatment, and (4) the dog may require hospitalization until symptoms improve if the owner does not wish to care for the dog after PPA withdrawal and/or after ADSC treatment.

Pre-Treatment Examination

Before treatment, all dogs undergo physical examination, routine clinical chemistry and hematology evaluation, and urinalysis to ensure that the subjects are healthy overall and free of primary urinary tract infection. In addition, the test injection site in the hind leg will be examined so as to ensure the lack of inflammation.

Treatment Procedure

In this study, the treatment procedure for UI is injection of 1-10 million porcine ADSC into the sphincter area of the urethra. Precision injection is accomplished with an uroscope that enables both visualization and injection. The volume of the suspension and the number of cells vary proportionally to the weight of the subject. For example, a 20-kg dog will receive 2 million ADSC in 0.2 ml PBS per injection. Generally, 5 million cells per 10 kg of body weight is used.

Post-Treatment Evaluations

Owner's evaluation will be conducted on a daily basis by observing the following characteristics: monitoring the site of injection for signs of reaction such as redness, pain, and heat, monitoring the animal for signs of anaphylactic reaction and urinary blockage, any other unusual signs in the animal, such as persistent nausea, fatigue, lethargy, decreased appetite and difficult urination.

The veterinarian's evaluation is conducted at 10-15, 25-30 and 55-60 days after treatment.

Example 2

Use of ADSC for Treatment of Osteoarthritis

Treatment Procedure

While OA can afflict virtually any joints, it is most frequently associated with the stifle and hip joints. Injection of ADSC into these joints is similar to injection of corticosteroids, except that a cell suspension is used instead of the steroid. The volume of the cell suspension and the number of cells vary proportional to the size of the subject. As an example, a 20-kg dog will receive 5 million ADSC in 0.5 ml PBS per joint. Following the treatment, owners are counseled to leash-walk their dogs 30 minutes daily. Any oral medications that the dog are taking prior to ADSC treatment are allowed to continue. Any intraarticular treatments prior to ADSC treatment should discontinue.

Post-Treatment Ealuation

Veterinary evaluation will incorporate history, physical examination, and lameness examination including joint mobility and notation of pain on manipulation. Clinical outcome measures will be based on veterinary orthopedic evaluation using a numerical rating scale based on a standardized questionnaire. Baseline results for both owner and veterinary evaluations will be recorded between 2 and 14 days before the dogs receive either the test or control preparation by intraarticular injection. Follow-up visits to the veterinary clinic will be required at 30, 60, and 90 days after the dog's intraarticular injection. At each visit, owners will be asked to complete a numeric rating scale (1 (best) to 5 (worst)) as part of a standard questionnaire adapted from the Cincinnati Orthopedic Disability Index, which include evaluation of the following parameters: walk, run, jump, turning suddenly, getting up from lying down, lying down from standing, climbing stairs, descending stairs, squatting to urinate or defecate, stiffness in the morning, stiffness in the evening, difficulty walking on slippery floors, and willingness to play voluntarily.

Example 3

Treating a Non-Human Mammal with Diabetes with ADSC

Pdx1 is a key regulatory gene in beta cell (insulin producing cells) development and PV-16 is an engineered version of Pdx1 (see, e.g., Tang et al., *Laboratory Investigation* 86:829-841 (2006); Cao et al., *Diabetes* 53:3168-3178 (2004); Tang et al., *Laboratory Investigation* 86:83-93 (2006)). This Example describes results showing that, after transfection with Lentivirus carrying the Pdx gene or PV-16, ADSCs can be transformed into insulin-producing cells. These cells can be then injected to the portal vein (as in islet cell transplantation) to help diabetic subjects. Approximately 1 billion cells are needed for this treatment.

Non-human ADSCs are transfected with Lenti-Pdx1, Lenti-PV-16, or Lenti-GFP (GFP, green fluorescence protein), with the latter serving as a negative control. After transfection, the cells are cultured in differentiation medium. After 21 days, the morphology of GFP-transfected cells remained unchanged while that of Pdx1- or PV-16-transfected cells changed significantly. In addition, the Pdx1- or PV-16-transfected cells appeared to be secreting granular materials. Pdx1 mRNA expression by the transfected cells is confirmed and measured by RT-PCR. Western blots are used to confirm expression of the Pdx1 protein.

The production of insulin by transfected cells is also analyzed by staining cells with an anti-insulin antibody.

Example 4

Method for Isolating ADSC Using Recycled Collagenase

Isolated adipose tissue (i.e., fat tissue or liposuction fat) from non-human mammals was rinsed with PBS containing 1% penicillin and streptomycin, minced into small pieces, then mixed with a solution containing 0.075% collagenase Type IA (Sigma-Aldrich, St. Louis, Mo.) at 5:1 v/v ratio of collagenase solution:adipose. After incubation for 1 hour at 37° C. with vigorous shaking, the product was then centrifuged at 220×g for 10 minutes at room temperature. Three layers were formed: the upper lipid layer, the middle collagenase layer and the bottom cellular pellet. The middle layer was collected and filtered through a 200 μm filter followed by centrifugation. The recycled collagenase Type IA in the flow-thru, is used to digest fresh adipose tissue (also decreasing the cost of purchasing large amount of collagenase), using a higher ratio (7:1, by volume) than the first round.

Example 5

Preserving ADSC with Superoxide Dismutase

This Example describes a new adipose tissue preservation solution (ATPS) containing superoxide dismutase isolated from mammalian erythrocytes to preserve cell viability. The ATPS consists of 200 mg/L $KH_2PO_4$, 200 mg/L KCl, 2.16 g/L $Na_2HPO_4.7H_2O$, 8 g/L NaCl, 30,000 units/L Superoxide Dismutase (SOD), and 5 g/L bovine serum albumin (BSA).

The ATPS was used to preserve the adipose tissue at 4° C. for 24 and 48 hr. The preserved adipose tissues were used to isolate adipose derived stem cells according to the procedure described above. The yield of adipose-derived stem cells obtained from the ATPS-preserved issue and freshly harvested adipose tissue from two subjects was compared. The yield of ADSC was 85% at 24 hours and 65% at 48 hours as compared to freshly harvested adipose tissue. This is much better than the yields obtained without ATPS as reported by Matsumoto et al., *Plast. Reconstr. Surg.* (2007) 120(6):1510-7.

The ATPS has also been tested for preservation of adipose stem cells. $1 \times 10^6$ non-human adipose derived stem cells were mixed with 1 ml of ATPS and stored at 4° C. After 48 hours, a cell viability test (the trypan blue method) was performed. The results indicated that less than 5% of cells were damaged after 48 hours of preservation with ATPS.

Example 6

Method for Isolating a Preferred Population of ADSC

Efficient and accurate separation of specific cell types is a crucial aspect of many research projects. The use of antibodies for cell separation is not a new technique. "Panning," an immuno-selection method used to enrich a specific cell population from a diverse mixture of cell types, has been around for quite some time. This method is based on the selective capabilities of antibodies bound to cell culture dishes. A mixture of cell types is cultured on the antibody-coated plates and allowed to bind for a short period of time. The non-adherent cells (those that do not bind antibody) can then be gently eluted from the culture dish allowing bound cells to be harvested. This method facilitated the development of other new technologies such as density-gradient separations and methods that exploit unique surface binding properties of specific cell types. The development of magnetic bead technology allowed repetitive washing of bead-bound cells, greatly improving the potential purity of separations. The size and composition of the paramagnetic beads utilized by various companies varies significantly and further refinements/improvements have been regularly forthcoming.

The stromal vascular fraction derived from adipose tissue digestion consists of many types of cells, such as stem cells, endothelium, smooth muscle cell, and other terminally differentiated cells. The magnetic cell system provides excellent sorting of magnetic-bead-labeled cells.

Freshly isolated ADSC were analyzed by flow cytometry for cell surface antigen expression according to the manufacturer's protocol. The cells were incubated with primary antibody (Table 1) in 50 μl wash buffer (PBS containing 1% FBS and 0.1% $Na_3N$) for 30 minutes on ice, followed by another incubation with FITC-conjugated secondary antibody (goat anti-IgG). The cells were then rinsed twice with wash buffer, fixed with 1% para-formaldehyde in PBS, and analyzed by a fluorescence-activated cell sorter (FACS Vantage SE; Becton Dickinson). The results were analyzed with FlowJo software (Tree Star, Inc., Ashland, Oreg.). Cell antigens analyzed were CD13, CD31, CD34, CD90, CD105, CD133, SSEA-1, and telomerase. The expression levels are presented in Table 2.

TABLE 1

Antibodies Used in This Study

| Target protein | Supplier |
| --- | --- |
| CD13 | Santa Cruz Biotech, Santa Cruz, CA |
| CD31 | Santa Cruz Biotech, Santa Cruz, CA |
| CD34 | Santa Cruz Biotech, Santa Cruz, CA |
| CD90 | Santa Cruz Biotech, Santa Cruz, CA |
| CD105 | Chemicon, Temecula, CA |
| CD133 | Abcam Inc, Cambridge, MA |
| SSEA1 | Abcam Inc, Cambridge, MA |
| Telomerase | Abeam Inc, Cambridge, MA |

TABLE 2

Expression level of cellular markers in adipose derived stem cells

| Cellular markers | Positive % (mean ± standard deviation) |
| --- | --- |
| CD13 | 6.5 ± 1.1 |
| CD31 | 24.1 ± 3.8 |
| CD34 | 67.9 ± 20 |
| CD90 | 87 ± 21.4 |
| CD105 | 56 ± 18.6 |
| CD133 | 6.9 ± 2.5 |
| SSEA1 | 25.7 ± 6.9 |
| Telomerase | 2.7 ± 0.98 |

Antibody Cocktail

According to the result of flow cytometry, three markers were selected as positive cellular markers to separate the adipose derived stem cells. The antibody cocktail include mouse anti-CD34, mouse anti-CD90 and mouse anti-SSEA1 in a ratio of 2:3:5.

Positive Selection of CD34(+)/CD90(+)/SSEA1(+) by MACS

Non-human adipose derived stem cells were incubated with CD34 (+)/CD90 (+)/SSEA1 (+). Positive cells were selected with Pan-mouse antibody magnetic beads.

Differences in proliferation: CD34(+)/CD90(+)/SSEA1(+) versus CD34(−)/CD90(−)/SSEA1(−) cells The positive cells selected using the CD34(+)/CD90(+)/SSEA1(+) cocktail and the negative depleted cells were cultured and used for the cell proliferation assay by the MTT test. The result showed that the positive cell grow faster than the negative selected cell.

Difference in Cytokine Secretion: CD34 (+)/CD90(+)/SSEA1(+) Versus CD34(−)/CD90(−)/SSEA1(−) Cells The cell culture medium from positive and negative selected cells was used to check the production of cytokines by the cytokine arrays. The result indicated that positive selected cell secrete more cytokines, such as MCP1, b-NGF, TIMP-1 TNF-a, IL-1b, CINC-1 et al.

Difference in Recovering Erectile Function In Vivo: CD34 (+)/CD90(+)/SSEA1(+) Versus CD34(−)/CD90(−)/SSEA1 (−) Cells The positive and negative selected ADSCs were cultured and injected into rat corpus cavernosum after crush injury of the cavernous nerves. Four weeks later, erectile function was assessed by neurostimulation. The results showed that the positively selected cells significantly improved the erectile function while the negative cells did not.

Example 7

Culturing ADSCs in Platelet Lysates

In most of the standard culture media for ADSCs, animal serum is an essential component. However, integration of animal protein into the stem cells has been reported and this is a major concern in human cell therapy. Here we describe a novel method for culturing ADSCs in a platelet lysate medium.

Platelet lysate was obtained from whole blood according to the following procedure. Whole blood was drawn into four 50 ml sterile plastic tubes containing sodium citrate dehydrate, and centrifuged at 350×g for 10 minutes. The platelet-rich plasma fraction was washed with an equal volume of Phosphate Buffer saline (PBS) containing 0.38 mg/ml of sodium citrate dihydrate. Platelets were then centrifuged at 510×g for 10 minutes and the pellet was suspended in DMEM to a final concentration of $1-2 \times 10^9$ cells/ml. Platelet lysis, (and consequent release of chemotactic and growth factors) was obtained by a single cycle of freezing (80° C.) and thawing (37° C.). The platelet lysate in DMEM was centrifuged at high speed (12,000×g, 10 minutes.) to remove cell membranes, and the supernatant was extracted and stored at −80° C.

To test the ability to maintain and promote cell growth and proliferation, ADSCs were cultured in serum free medium, and in medium containing 10% FBS, 2% platelet lysate and 4% platelet lysate. The proliferative effect of platelet lysate on ADSC was evaluated by the MTT test. The result indicated that 4% platelet lysate has the same effect in supporting cell growth and proliferation as 10% FBS.

Example 8

The Use of 60 Micron PLGA Microspheres and Carboxymethylcellulose as Carriers for ADSC An injectable poly(lactic-co-glycolic acid) ("PLGA") solution was prepared by first mixing 1 µg of 60-µm PLGA microspheres with 1 ml of 0.5% carboxymethylcellulose (CMC), dissolved in PBS). Approximately $5 \times 10^6$ ADSCs were mixed with 1 ml of this PLGA/CMC mixture. After incubating on ice for 30 minutes, the ADSCs/PLGA mixture was injected into the urethra. As a control, ADSCs mixed with saline were injected to a different group of animals. Four weeks later, the animals were killed and tissues and examined. The results showed that many more ADSCs were retained in the injected area in the ADSC/PLGA group than the saline group.

Example 9

Treating Wounds and Other Conditions with ADSC

The degree to which ADSCs could spontaneously differentiate into blood vessels was assessed. For example, ADSCs were injected percutaneously into the subcutaneous space in healthy rats. Histological studies showed that the ADSCs differentiated into a wide variety of local cell types, including blood vessels, fat, muscle, connective tissue/fibroblasts, and peri-follicular (surrounding a skin hair follicle) cells.

ADSCs were also injected subcutaneously along the suture site of a surgical wound. One side of the suture line received subcutaneous injection of ADSC suspended in buffer, whereas the other side received only injection of buffer. Results showed that the side of the wound that received ADSC developed a significantly greater density of blood vessels. Furthermore, the degree of scar formation on the side of the wound that received ADSC appeared more attenuated as compared to the control side. Such experiments were repeated wherein the design was varied so that identical wounds were created in the same animal, and the experimental wound received ADSCs while the control wound, otherwise identical, received no ADSCs. The results were highly reproducible.

Additional studies showed that injected ADSCs preferentially differentiate into blood vessels within a wound environment. A reagent called Matrigel was used to introduce the ADSCs into the wound environment. Matrigel is a biocompatible but otherwise inert material that serves as a dense gel which allows diffusion of oxygen and micronutrients, but which is sufficiently dense to prevent local tissue or cell ingrowth. Importantly, it exists in a liquid state at artificially cold temperatures, and in a semi-solid state at body temperature.

In the experimental group, ADSCs were suspended within a set volume of Matrigel, and then percutaneously injected the Matrigel into the subcutaneous space of a rat's dorsal hump. In the same rat, on the contralateral side of their dorsal hump, we injected an identical volume of Matrigel, without ADSC, as a control. The Matrigel was allowed to remain within the wound site for 10 days, and then the Matrigel was excised from the wound space, sectioned, and histology was evaluated. Results showed that the labeled ADSC suspended in the Matrigel differentiated into blood vessels/endothelial cells. Furthermore, the edges of the Matrigel in apposition to the wound cavity demonstrated a greater density of blood vessels, as compared to the center. Again, the ADSC were labeled with a nuclear marker, which confirmed that the neovascularity visualized corresponded to ADSC, not local blood vessel ingrowth. The control injections of Matrigel demonstrated no blood vessel formation.

The results described above show that the host tissue environment within the target site influences the types of cells that result from the differentiation of ADSCs. Injected ADSCs respond to a wound environment by differentiating preferentially into blood vessels, which is consistent with the natural wound healing response, i.e., local tissue hypoxia influences ADSCs to differentiate preferentially into blood vessels. Furthermore, ADSCs appear to spontaneously differentiate into the other cell types that comprise the natural wound healing apparatus, e.g., fibroblasts and inflammatory cells. Specific wound applications include, without limitation, the prevention of scarring/stricture at surgical anastomoses, radiation-induced wounds, surgical stomas (e.g., colostomies, urostomoies), and cosmetic surgical wounds. ADSC treatment can also be used to prevent the development of pressure-sores (decubitus ulcers) or promote the healing of existing pressure-sores.

Example 10

Additional Materials and Methods

ADSC Isolation and Culture

Isolation of rat ADSC was perfomed as described in Ning H, et al. *Differentiation* 74:510-518 (2006).

Lentiviral Transduction

Lentiviral constructs containing mouse Pdx1, Pdx1-PV-16 (PV-16, a genetically modified form of Pdx1), or green fluorescence protein (GFP, as control) have been described. See, e.g., Tang D Q, et al, *Lab. Invest.* 86:829-841 (2006) and Tang D Q, et al., *Lab. Invest.* 86:83-93 (2006). These constructs were transduced into ADSC overnight at a multiplicity of infection (MOI) of 20. After two days of recovery, the transduced cells were switched to differentiation medium (DMEM with 23 mM glucose), grown to confluence, and split 1:3 to approximately $5 \times 10^5$ cells per 10-cm dish. They were thereafter split 1:3 every 7-10 days.

Measurement of Insulin Secretion

For the measurement of static insulin secretion, human ADSC lines transduced with GFP, Pdx1 or PV-16 were cultured in differentiation medium (20 mM glucose) with FBS for 3 weeks. The cell culture medium was then collected and analyzed with a commercial ELISA kit for human insulin (Cat #EZHIASF-14K, Linco Research, St. Charles, Mo.). For the measurement of insulin secretion in response to glucose challenge, cells grown in a 6-well plate ($6 \times 10^4$ cells/well) were washed with PBS 3 times and then incubated in KRB buffer (120 mM NaCl, 2.5 mM $CaCl_2$, 1.1 mM $MgCl_2$, 25 mM $NaHCO_3$, and 0.1% BSA) for 1 h. Glucose was then added to final concentrations of 0, 5.6, 16.7, 23, and 33 mM. After another hour of incubation, the KRB buffer was collected and analyzed with a commercial ELISA kit for rat insulin (Cat #EZRMI-13K, Linco Research, St. Charles, Mo.). These experiments were done in triplicate.

Establishment of Type 1 Diabetic Rat Model

Streptozotocin (STZ) is known to selectively destroy pancreatic (3-cells (Mansford K R et al, *Lancet* 1:670-671 (1968)) and has been used to establish a type 1 diabetic rat model (El-Sakka A I, et al., *Int J Impot Res* 11:123-132 (1999). Two-month-old female Sprague-Dawley rats were made hyperglycemic by intraperitoneal injection of 60 mg of STZ (in 20 mM citrate buffer) per kg of body weight. Control rats were injected with 20 mM citrate buffer. Afterwards, body weight and blood glucose levels were monitored weekly with samples obtained from the tail vein using Accutrend strip (Roche Diagnostics, Indianapolis, Ind.). When blood glucose reached 300 mg/dl (in ~7 days), the STZ-treated rats were subjected to injection with IP-ADSC or saline under the renal capsule.

Cell Transplantation Under Renal Capsule

Rats were anesthetized by exposure to 1-3% isoflurane, and a 2-cm incision was made through the skin and muscle of the left flank. The wound was rinsed with 1 ml PBS containing penicillin/streptomycin), and the kidney was externalized. A small lateral cut was made in the capsule, and $2 \times 10^6$ IP-ADSC in 1 ml PBS or PBS only was dispensed beneath the capsule. The kidney was returned to the abdominal cavity, and the incision closed using surgical clips. The injection site was marked with a 7-0 nylon suture for identification.

Glucose Tolerance Test

Intraperitoneal glucose tolerance testing (IPGTT) was performed as described by the Animal Models of Diabetes Complications Consortium (www.amdcc.org). Rats were fasted for 7 hours and then injected intraperitoneally with 1 mg of glucose in saline per gram of body weight. Blood glucose levels were monitored for 2 hours at 30-minutes intervals in samples obtained from the tail vein.

Immunocytochemistry and Fluorescence Microscopy

Cells were seeded onto a coverslip inside each well of a 6-well plate at 40-60% confluence in DMEM. The next day, the cells were rinsed with PBS and fixed with ice-cold methanol for 5 minutes. The cells were rinsed with PBS again and permeabilized with 0.05% triton X-100 for 8 minutes. After another PBS rinse, the cells were incubated with 5% horse serum for 1 hour and then with anti-insulin antibody (Abcam Inc., Cambridge, Mass., 1:500) for 1 hour. After 3 rinses with PBS, the cells were incubated with Texas red-conjugated secondary antibody (Jackson ImmunoResearch Laboratories, West Grove, Pa.) for 1 hour. After 3 rinses with PBS, the cells were stained with 4',6-diamidino-2-phenylindole (DAPI, for nuclear staining, 1 µg/ml, Sigma-Aldrich, St. Louis, Mo.) for 5 minutes. The stained cells were examined with Nikon Eclipse E600 fluorescence microscope and the images recorded with Retiga 1300 Q-imaging camera.

Histology and Immunofluorescence

Tissue samples were fixed in cold 2% formaldehyde and 0.002% saturated picric acid in 0.1 M phosphate buffer, pH 8.0, for 4 hours followed by overnight immersion in buffer containing 30% sucrose. The specimens were then embedded in OCT Compound (Sakura Finetic USA, Torrance, Calif.) and stored at -70° C. until use. Fixed frozen tissue specimens were cut at 10 microns, mounted onto Super-Frost-Plus charged slides (Fisher Scientific, Pittsburgh, Pa.) and air dried for 5 minutes. These slides were stained with hematoxylin and eosin (HE staining) for general histological examination. For immunofluorescence examination, the slides were placed in 0.3% $H_2O_2$/methanol for 10 minutes, washed twice in PBS for 5 minutes and incubated with 3% horse serum in PBS/0.3% Triton X-100 for 30 minutes at room temperature. After draining this solution from the tissue section, the slides were incubated overnight at 4° C. with anti-insulin antibody (Abcam Inc., Cambridge, Mass., 1:500) for 1 hour. Control tissue sections were similarly prepared except no primary antibody was added. After rinses, the sections were incubated with Texas red-conjugated secondary antibody (Jackson ImmunoResearch Laboratories, West Grove, Pa.) followed by staining with 4',6-diamidino-2-phenylindole (DAPI, for nuclear staining, 1 µg/ml, Sigma-Aldrich, St. Louis, Mo.).

Western Blot Analysis

Cells were lysed in buffer containing 1% IGEPAL CA-630, 0.5% sodium deoxycholate, 0.1% SDS, aprotinin (10 µg/ml), leupeptin (10 µg/ml), and PBS. Cell lysates containing 20 µg of protein were electrophoresed in SDS-PAGE and then transferred to PVDF membrane (Millipore Corp., Bedford, Mass.). The membrane was stained with Ponceau S to verify the integrity of the transferred proteins and to monitor the unbiased transfer of all protein samples. Detection of protein on the membrane was performed with the ECL kit (Amersham Life Sciences Inc., Arlington Heights, Ill.) using anti-Pdx1 antibody (Santa Cruz Biotechnology, Santa Cruz, Calif.). The resulting images were analyzed with Chemilmager 4000 (Alpha Innotech Corporation, San Leandro, Calif.) to determine the integrated density value (IDV) of each protein band. Before re-probing with anti-b-actin antibody, the membrane was stripped in 62.5 mM Tris-HCl, pH 6.7, 2% SDS, 10 mM 2-mercaptoethanol at 56° C. for 30 minutes and then washed 4 times in 1× TB ST.

RT-PCR Analysis

Cells were homogenized in Tri-Reagent RNA extraction solution (Molecular Research Center, Cincinnati, Ohio). The extracted RNAs were further treated with DNase I to remove traces of contaminating DNA. Quantity and integrity of RNAs were examined by spectrophotometer and agarose gel electrophoresis, respectively. The RNAs were reverse-transcribed into a "library" of complementary DNAs (cDNAs) using SuperScript reverse transcriptase and its accompanying reagents (Invitrogen, Carlsbad, Calif.). Briefly, 2.5 µg of RNA were annealed to 0.4 µg of oligo-dT primer in a 12-µl volume. Four µl of 5× buffer, 2 µl of 0.1 M DTT, 1 µl of 10 mM dNTP, and 1 µl of reverse transcriptase were then added to bring the final reaction volume to 20 µl. After one hour of incubation at 42° C., the mixture was incubated at 70° C. for 10 minutes to inactivate the reverse transcriptase. Eighty µl of TE buffer were then added to make a 5× diluted library. A portion of this library was further diluted to various concentrations (up to 100× dilution). One µl of each dilution was then used in a 10-µl polymerase chain reaction (PCR) to identify the optimal input within the linear amplification range. In addition to the 1-µl diluted library, the PCR mixture consisted of 10 ng of each of a primer pair (Table 1) and reagents supplied with the Taq polymerase (Invitrogen). PCR was performed in DNA Engine (MJ Research, Inc., Watertown, Mass.) under calculated temperature control. The cycling program was set for 35 cycles of 94° C., 5 sec; 55° C., 5 sec; 72° C., 10 sec, followed by one cycle of 72° C., 5 minutes. The PCR products was electrophoresed in 1.5% agarose gels in the presence of ethidium bromide, visualized by UV fluorescence, and recorded by a digital camera connected to a computer.

Statistical Analysis

Data were analyzed with Prism 4 (GraphPad Software, Inc., San Diego, Calif.) and expressed as means±standard deviation. Student-t test was used to compare between two groups (e.g., treated and control). One-way ANOVA analysis of variance was used to compare among 3 or more groups. Differences with P<0.05 were considered significant.

Example 11

Characteristics of Human and Rat ADSC Cell Lines

Isolation and characterization of human and rat ADSC have been reported (Lin G, et al., *Stem cells and development* 17:1053-1063 (2008); Ning H, et al. *Differentiation* 74:510-518 (2006)). Adherence of freshly isolated cells to plastic culture dishes allowed the selection of morphologically homogeneous populations of ADSC lines. These adherent cells were fibroblastic in shape and grew at rate of about one doubling every 3 days. At the third passage, they were mostly negative for endothelial marker CD31 and for hematopoietic marker CD34. They also expressed very low levels of stem cell markers Oct4, SSEA1, and telomerase. However, despite the lack of obvious stem cell markers, both of these human and rat ADSC were capable of differentiating into endothelial and neuron-like cells (Ning H, et al. *Differentiation* 74:510-518 (2006); and Ning H, et al. FGF2 Promotes Endothelial Differentiation of Adipose Tissue-Derived Stem Cells. J Sex Med (In Press)).

Example 12

Figure 2:
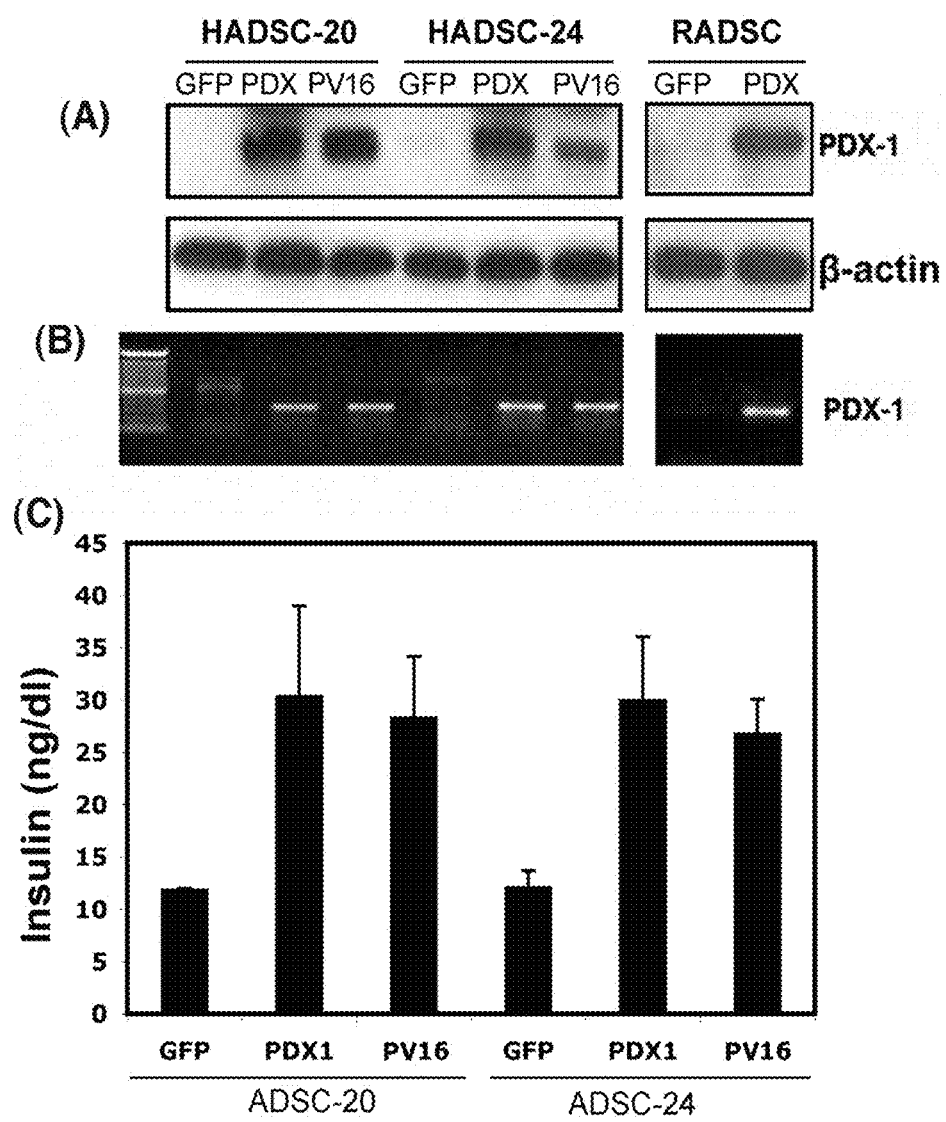
FIG. 2 depicts the results of experiments to verify of Pdx1 and insulin expression. Human and rat ADSC were transduced with GFP (control), Pdx1 or Pdx1-PV-16 (PV-16). Expression of Pdx1 in these cells was examined by western blotting (with (3-actin serving as control, Panel A) and RT-PCR (Panel B). Static insulin production by human ADSC (in DMEM with 23 mM glucose) was further examined by ELISA (Panel C).

Treatment of Type 1 Diabetes with Adipose Tissue-Derived Stem Cells (ADSC) Transduction and Expression of Pdx1 Gene in ADSC Two human and five rat ADSC lines were used as candidates for transduction with Pdx1. Additionally, the two human ADSC lines were also transfected with Pdx1-PV-16 (PV-16), which is a genetically modified form of Pdx1. Transduction with GFP served as a negative control as well as for the determination of transduction efficiency, which was found to be greater than 95% (percentage of cells displaying green fluorescence). One week after transduction the Pdx1- and PV-16-transduced cells, but not the GFP-transduced cells, exhibited a morphology suggesting the secretion of insulin granules (FIG. 1), which was subsequently confirmed by immunofluorescence staining (FIG. 1). RT-PCR and Western blot analyses also confirmed Pdx1 expression in Pdx1- and PV-16-transduced cells but not in GFP-transduced cells (FIG. 2). Finally, ELISA analysis showed the static production of insulin in Pdx1-transduced cells (FIG. 2); hence, insulin-producing ADSC (IPADSC).

Expression of Pdx1-Associated Genes in IPADSC

Figure 3:
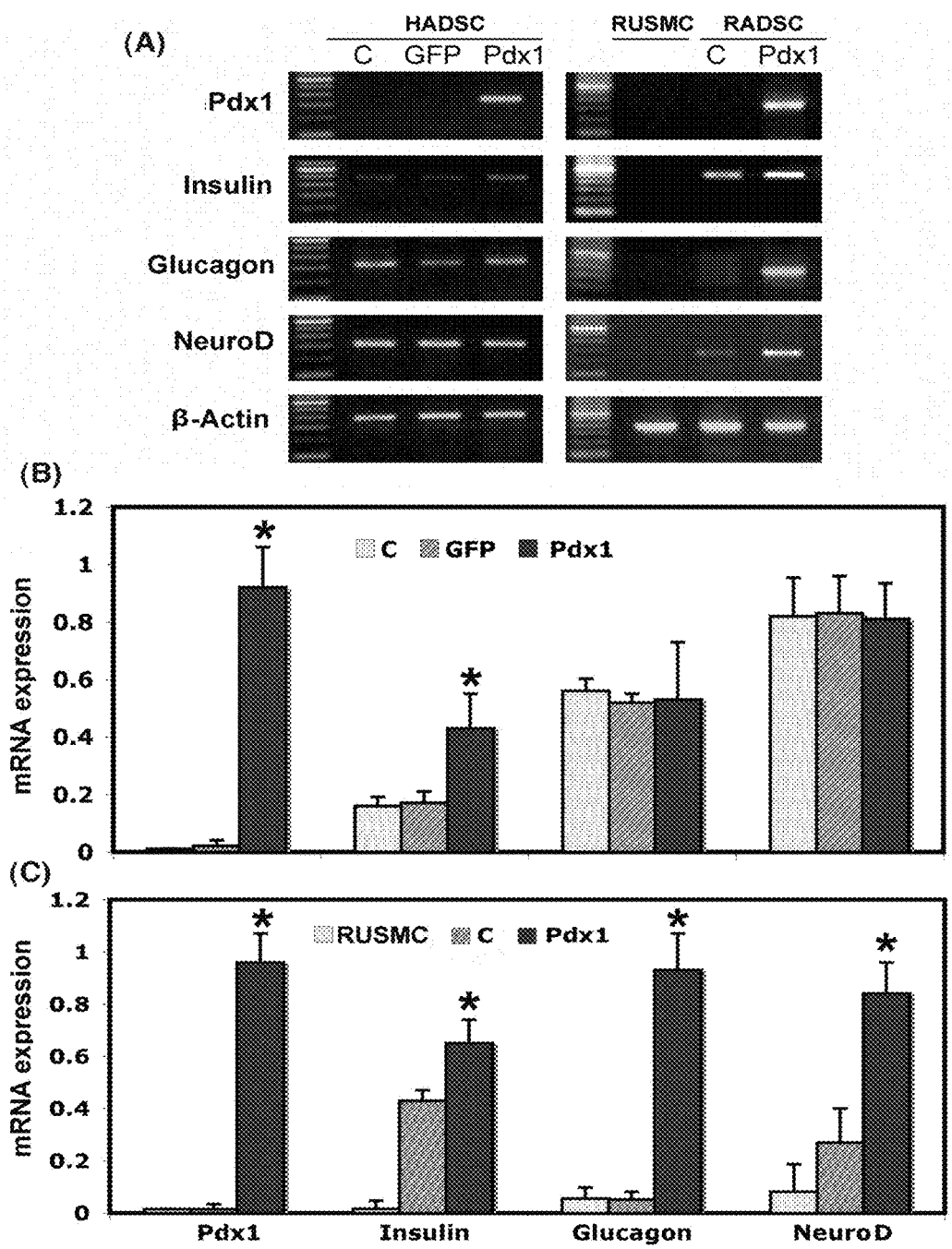
FIG. 3 depicts the results of experiments to examine pancreatic gene expression. Human and rat ADSC were untransduced (C) or transduced with GFP or Pdx1. These cells and rat urethra smooth muscle cells (RUSMC) were examined by RT-PCR for the expression of Pdx1, insulin, glucagon, and NeuroD (with b-actin serving as control, Panel A). Statistical analyses of the results for the human and rat cells are presented in Panels B (n=3) and C (n=5), respectively. Asterisks indicate significant differences (P<0.05) between Pdx1-transduced cells and untransduced cells.

Pdx1 controls the expression of several key genes during pancreatic development, including insulin, glucagon and NeuroD genes. RT-PCR analysis showed that human ADSC expressed glucagon and NeuroD constitutively (FIG. 3). They also expressed low levels of insulin, which were upregulated in IPADSC. Control rat ADSC expressed insulin, glucagon, and NeuroD at lower levels than IPADSC did. The specificity of expression of these three genes in control and IPADSC was confirmed by the lack of such expression in rat urethral smooth muscle cells (FIG. 3).

Increased Insulin Production in Response to Glucose Challenge

Figure 4:
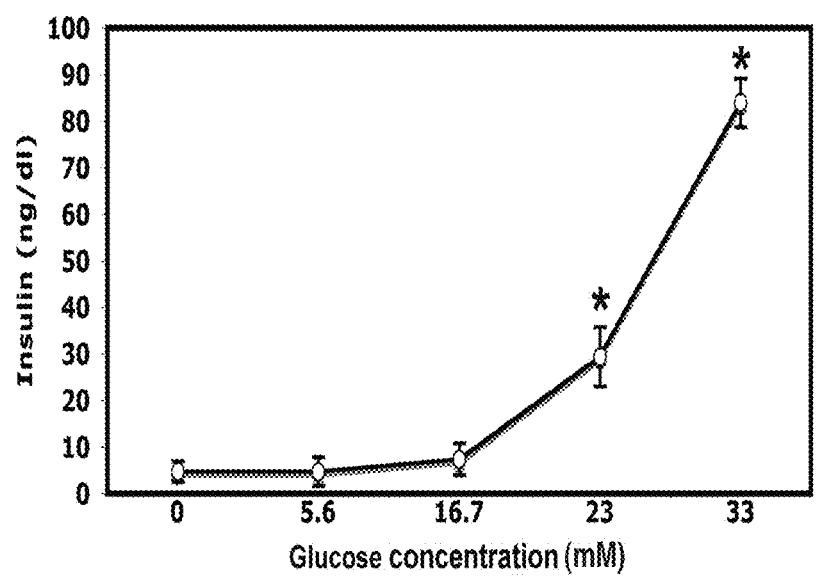
FIG. 4 depicts results of experiments on insulin production in response to glucose concentration. Pdx1-transduced cells were incubated in buffer containing the indicated concentrations of glucose. One hour later the amount of insulin in the buffer was assessed by ELISA. Asterisks indicate significant differences (P<0.05) as compared to insulin production at 0 mM of glucose.

As discussed above, Pdx1 transduction resulted in the generation of IPADSC, which released approximately 30 ng/dl of insulin into the culture medium (FIG. 2). Quantitative analysis showed that these cells produced increasing levels of insulin in response to increasing concentrations of glucose (FIG. 4).

Treatment of Diabetic Rats with IPADSC

Figure 5:
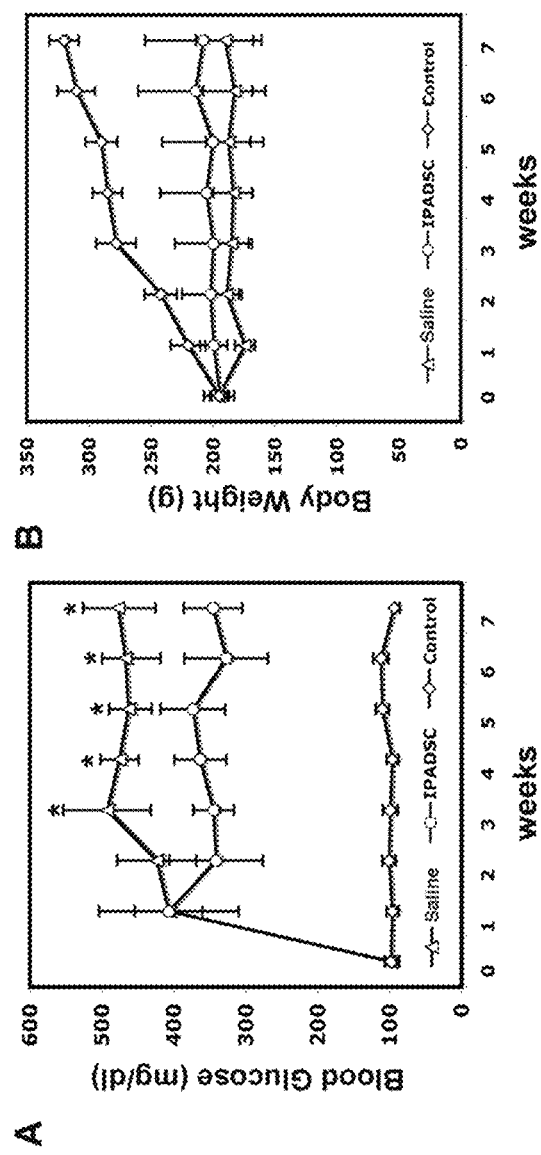
FIG. 5 shows the results of experiments for changes in blood glucose levels and body weight. Thirty rats were randomly and equally divided into 3 groups. The first group (Control) received intraperitoneal injection of 20 mM citrate buffer. The second and third groups both received intraperitoneal injection of 60 mg of STZ (in 20 mM citrate buffer) per kg of body weight. One week later the second group (Saline) received saline treatment while the third group (IPADSC) received IPADSC treatment. All rats were monitored weekly for body weight and fast blood glucose levels. Asterisks indicate significant differences (P<0.05) between IPADSC-treated and saline-treated rats.
Figure 6:
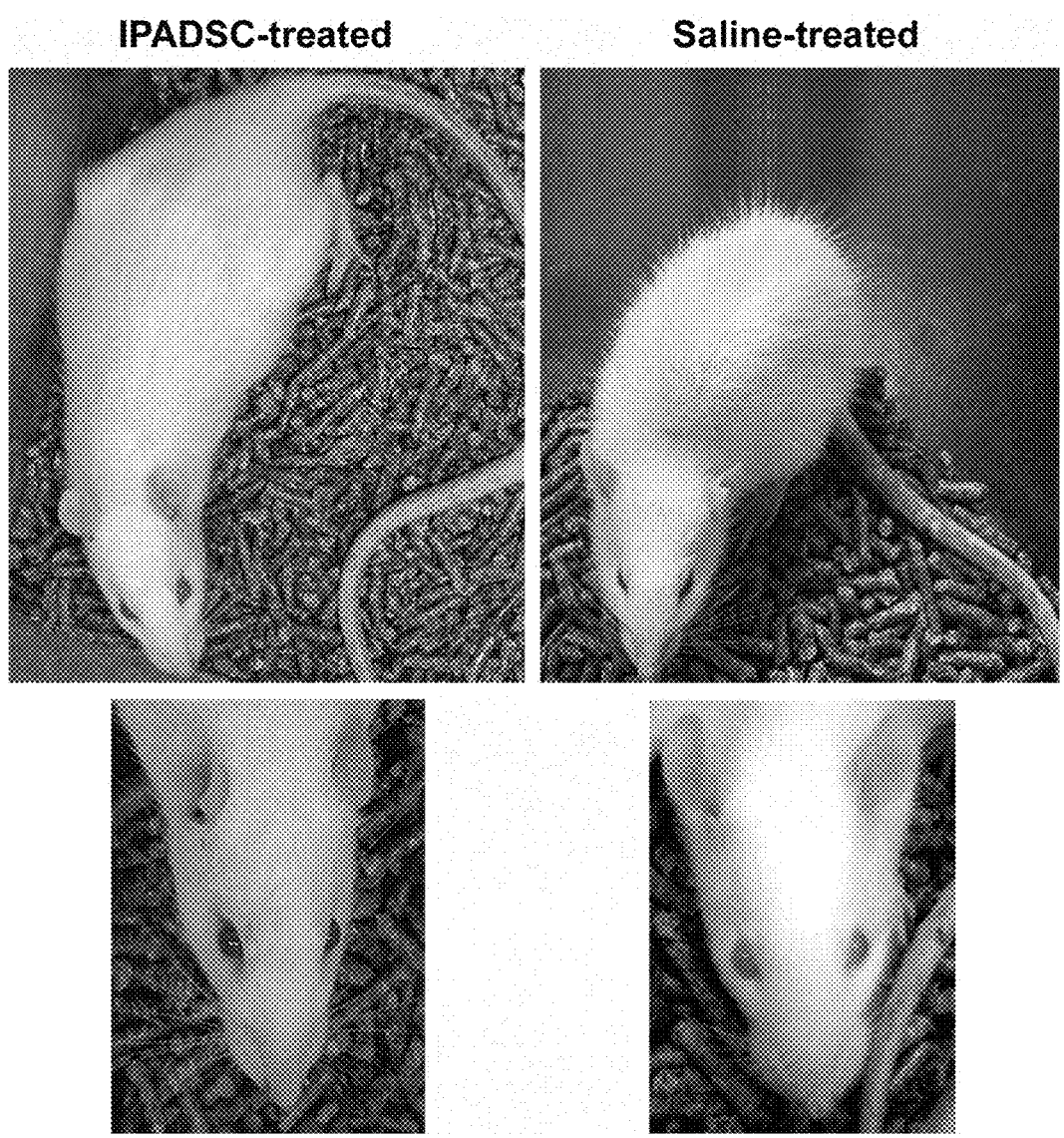
FIG. 6 depicts the changes in fur appearance and extent of cataract in rats.
Figure 7:
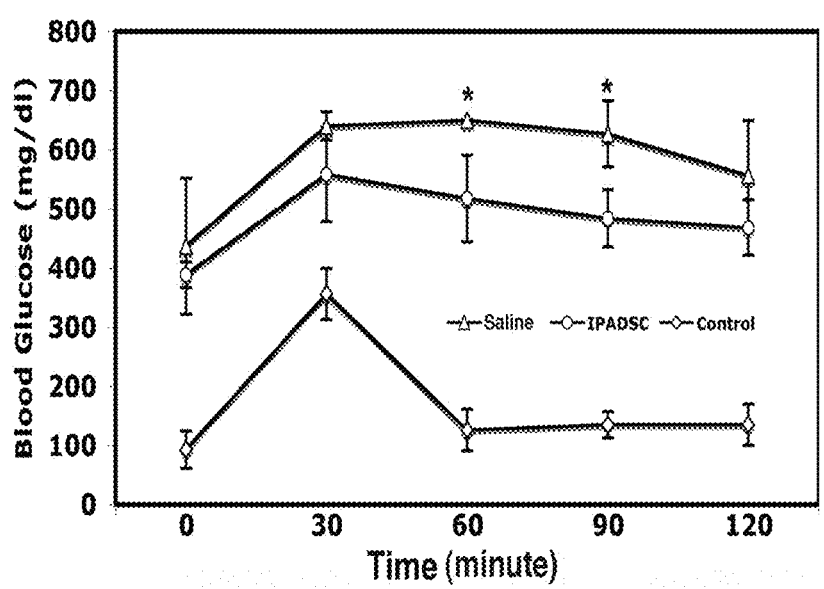
FIG. 7 shows results of experiments on glucose tolerance. At the end of the 7th week post-treatment, rats fasted for 7 hours received intraperitoneal injection of 1 mg of glucose per gram of body weight. Blood glucose levels were then monitored for 2 hours at 30-minutes intervals in samples obtained from the tail vein. Asterisks indicate significant differences (P<0.05) between IPADSC-treated and saline-treated rats.
Figure 8:
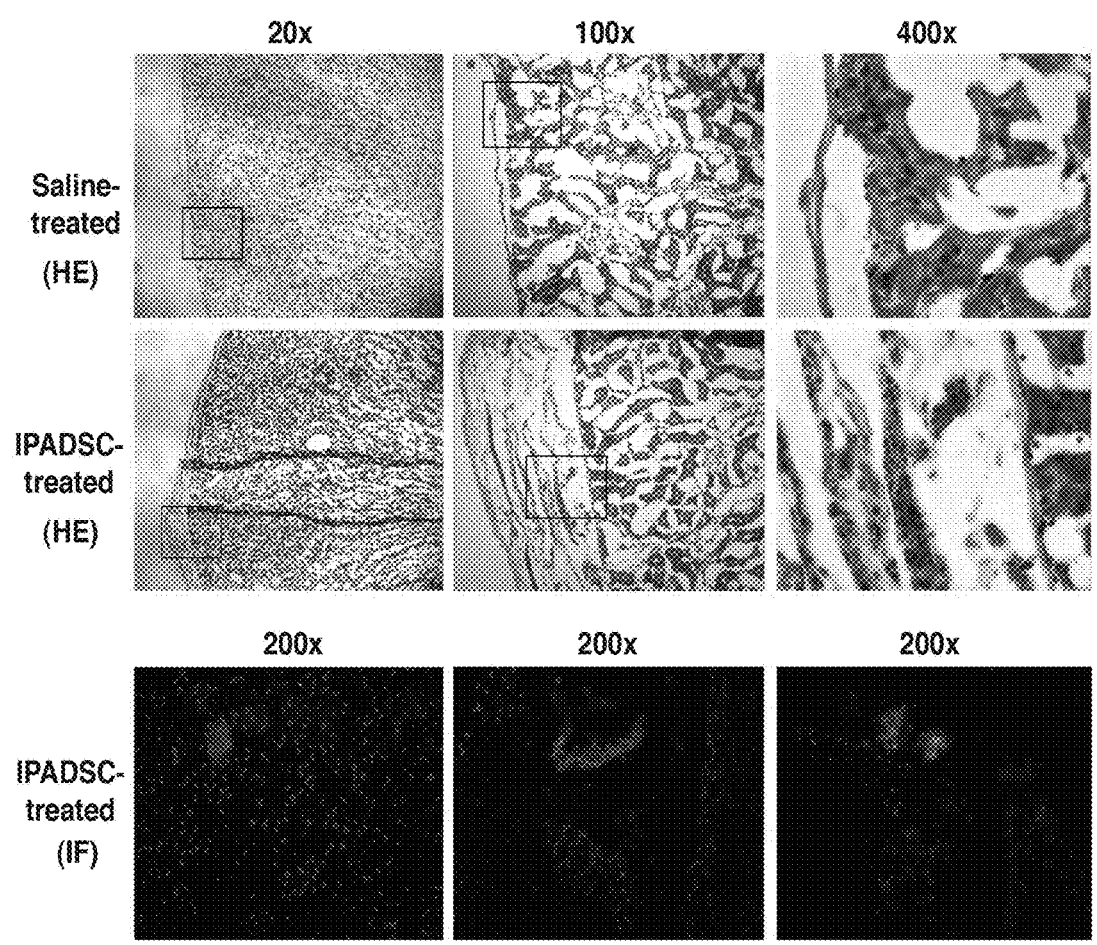
FIG. 8 shows the identification of transplanted cells. At the end of the 7th week post-treatment, rats were sacrificed and their kidneys harvested for histological examination. HE staining was used to examine the subcapsular space for the presence of transplanted cells. Immunofluorescence (IF) staining was used to identify cells expressing insulin. Boxed areas in the 20x photos are injection sites and are enlarged in the respective 100x photos. The boxed areas in the 100 x photos are further enlarged in the respective 400x photos. Note the tissue-like structures in the subcapsular space of the IPADSC-treated kidney. No such structure was visible in the saline-treated kidney. The IF photos were taken from 3 IPADSC-treated kidneys. Note the presence of insulin-positive cells.

Type 1 DM rats were established by intraperitoneal injection of STZ. One week after STZ injection, these rats had blood glucose levels in the range of 300 to 400 mg/dl, while control rats injected with citrate buffer only had normal blood glucose levels. Ten of the STZ-treated rats were subsequently treated with IPADSC while the other 10 STZ-treated rats were treated with saline. Treatment was done by transplantation of approximately 2 million rat IPADSC or injection of saline under renal capsule. These rats' fast blood glucose levels and body weight were then monitored weekly for 7 weeks. As shown in FIG. 5A, throughout the entire course IPADSC-treated rats had lower blood glucose levels than saline-treated rats (P<0.05). Body weights of IPADSC-treated rats were also better than those of saline-treated rats although the difference was not statistically significant (P>0.05) (FIG. 5B). At the end of the $7^{th}$ week, all rats were examined for fur appearance and extent of cataract, tested for glucose tolerance, and then sacrificed for histological assessment. The results showed that IPADSC-treated rats had healthier-looking (less scruffy) fur and lesser extent of cataract than saline-treated rats (FIG. 6). IPADSC-treated rats also had higher levels of glucose tolerance (FIG. 7). Finally, histological examination of the transplanted kidneys showed the presence of transplanted cells, which were stained positive for insulin (FIG. 8).

Example 13

Labeling and Tracking Stem Cell with EdU

Bromodeoxyuridine (5-bromo-2-deoxyuridine, BrdU) is a synthetic nucleoside that can be incorporated into the newly synthesized DNA of replicating cells. The BrdU-containing cells can be subsequently detected by immunochemistry using a BrdU-specific antibody. BrdU labeling method has been used mainly for analyzing cell cycle in cultured cells and for visualizing proliferating cells in the central nervous system. It has been also used to identify stem cells, which are believed to divide slowly or to segregate chromosomes asymmetrically, allowing the retention of BrdU in the slowly dividing stem cells or in the daughter (non-differentiating) stem cells but not in the differentiated daughter cells. In addition, BrdU labeling has been used to track stem or non-stem cells that are labeled in vitro and subsequently transplanted in vivo. In the case of stem cells, such tracking allows the determination of whether the transplanted stem cells have differentiated into a particular cell type.

Currently the method of choice to label dividing cells is the incorporation of the thymidine analogue, 5-bromo-2-deoxyuridine (BrdU), into the DNA of S-phase cells. After fixation of the labeled cells, BrdU is detected with a BrdU-specific antibody. However, BrdU immunochemistry can be problematic because strong DNA denaturing conditions, such as strong acids and heating, are required to reveal the epitope, which is masked within the DNA. This introduces significant variability within and between experiments. In an effort to overcome these problems, an alternative thymidine analogue, 5-ethynyl-2-deoxyuridine (EdU), was recently introduced. The terminal alkyne group of EdU allows detection using a fluorescent azide that covalently binds to the alkyne group. This detection method is fast and specific and does not require DNA denaturation. The aim was to investigate the feasibility of using EdU for labeling ADSC in vitro and for tracking the labeled cells in vivo.

Animals

All animal experiments in the study were approved by the Institutional Animal Care and Use Committee of University of California, San Francisco. A total of 12 pregnant three-month-old nulliparous Sprague-Dawley rats (Charles River Laboratories, Wilmington, Mass.) were randomly divided into two groups. One day before delivery, 200 µg EdU in PBS were injected (i.p.) in the test group and PBS only in the control group. The newborn rats were used to track the EdU labeling in vivo. One week after the delivery, adipose tissues were harvested from the adult rats for the isolation of ADSC, which were subsequently used for tracking EdU-labeled cells in vivo.

EdU Labeling

Figure 9:
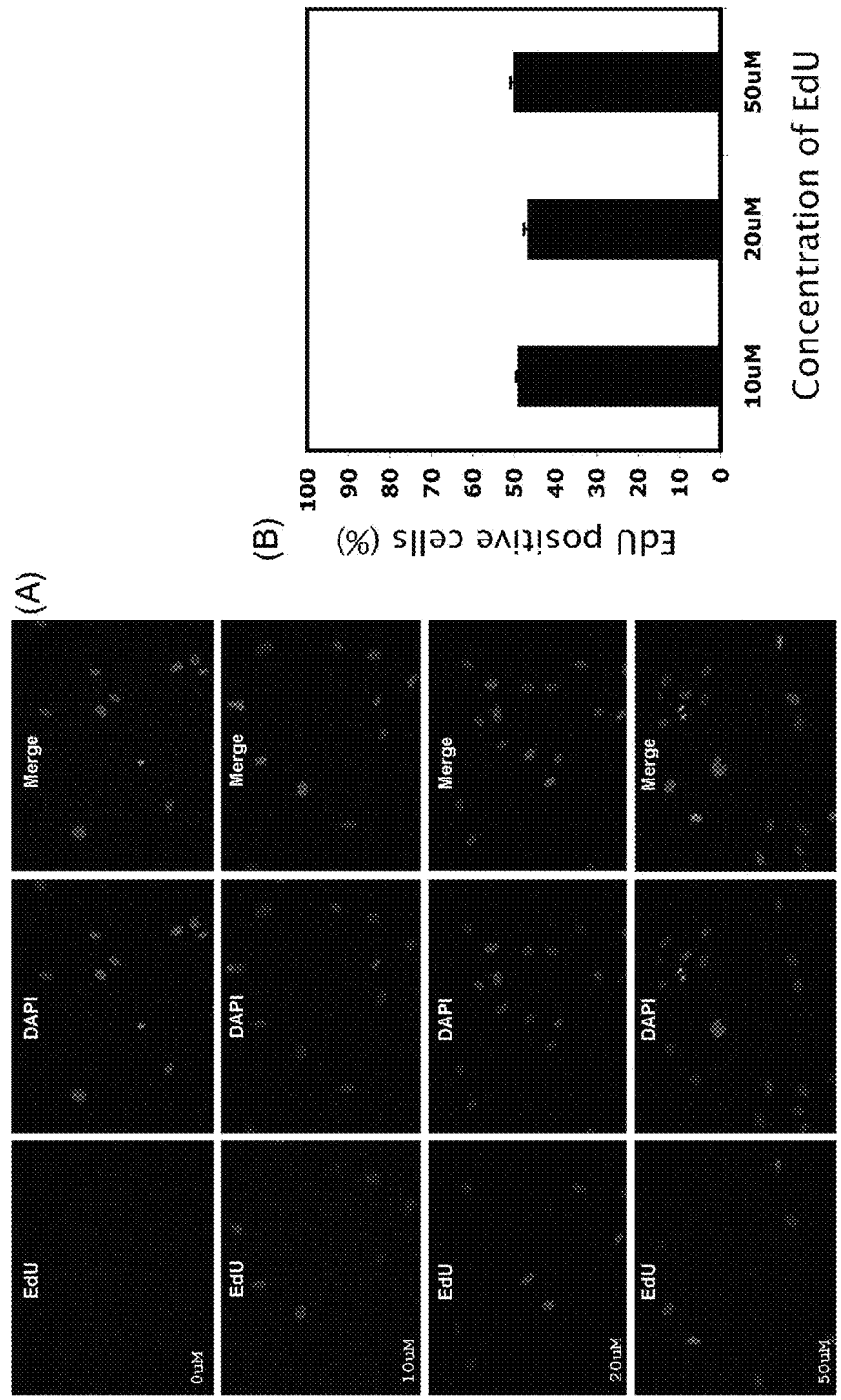
FIG. 9 depicts dosage effect. EdU was added to ADSC at 0, 10, 20, and 50 μM. Cellular location was identified by DAPI staining of the nucleus (which would be blue if color photos were used). EdU was detected by Alexa 594 (which would be red if color photos were used). The results show that approximately 50% of cells were EdU-labeled (A, ×200) regardless of EdU concentration (B, P>0.05).
Figure 10:
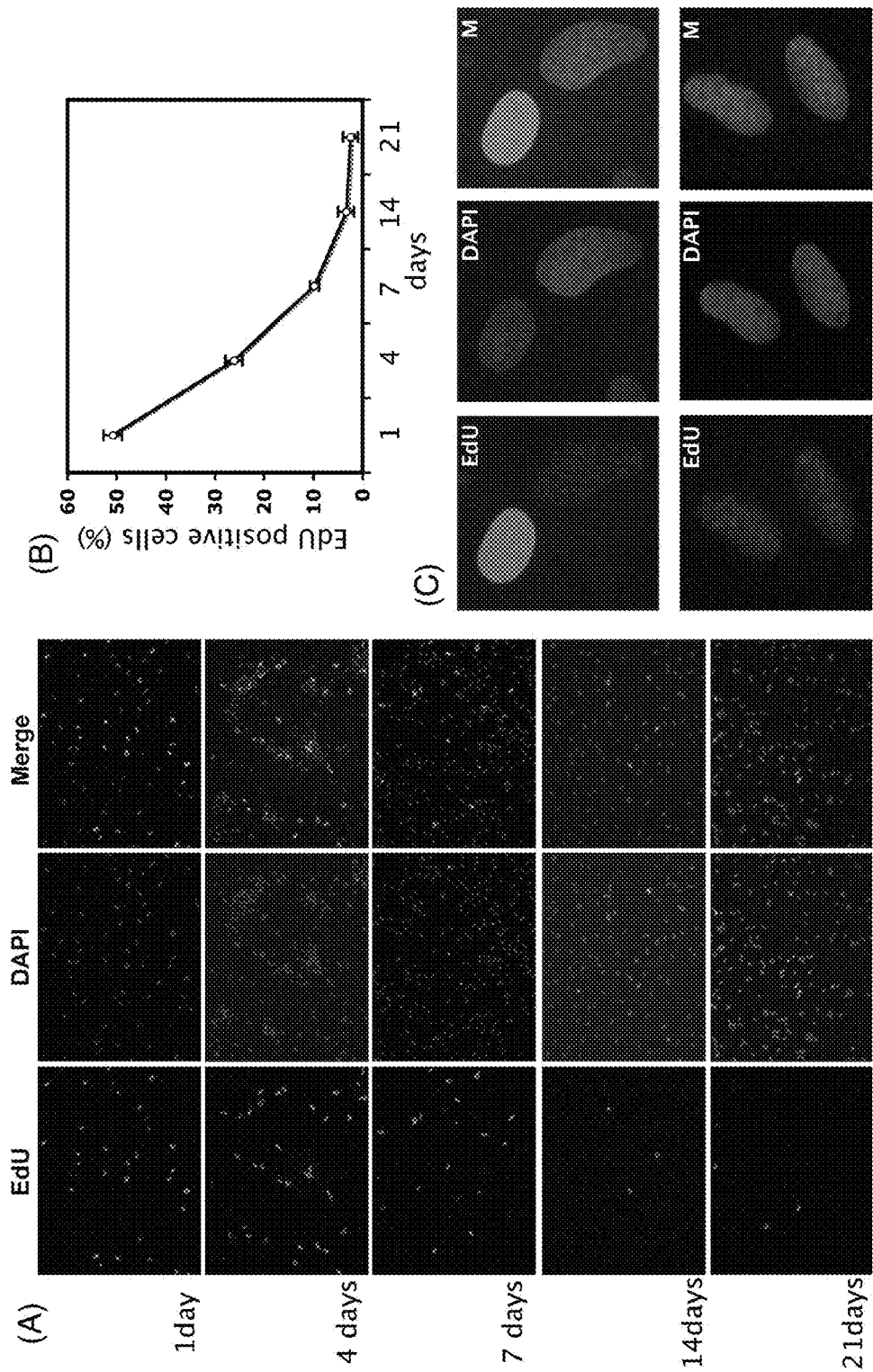
FIG. 10 show the results of a time-course study. ADSC were labeled with 10 μM EdU and then split at 1 day, 4 days, 7 days, 14 days, and 21 days. The results show that EdU signal in the positively labeled cells decreased with time (A, ×100; B, P<0.01). Higher magnification (1000×) of cells at day 21 is shown in panel C.

ADSCs were grown on glass coverslips in DMEM supplemented with 10% bovine calf serum, penicillin, and streptomycin. For dosage effect, EdU was added to the culture media at 0, 10, 20 and 50 µM. Twenty-four hours later, cells were washed with PBS followed by addition of regular culture media (FIG. 9). For time-course study, ADSC were labeled with 10 µM EdU and then split at 1 day, 4 days, 7 days, 14 days and 21 days (FIG. 10).

EdU Staining

After methanol fixation, cells were washed twice with PBS and then incubated in 3% BSA in PBS followed by 0.5% Triton® X-100 in PBS for 20 minutes at room temperature. The cells were then incubated with freshly made Click-it reaction cocktail (Invitrogen) for 30 minutes at room temperature in the dark. Cells were counterstained with DAPI, mounted in standard mounting media and imaged by fluorescence microscopy.

EdU Labeling of Tissues

Figure 11:
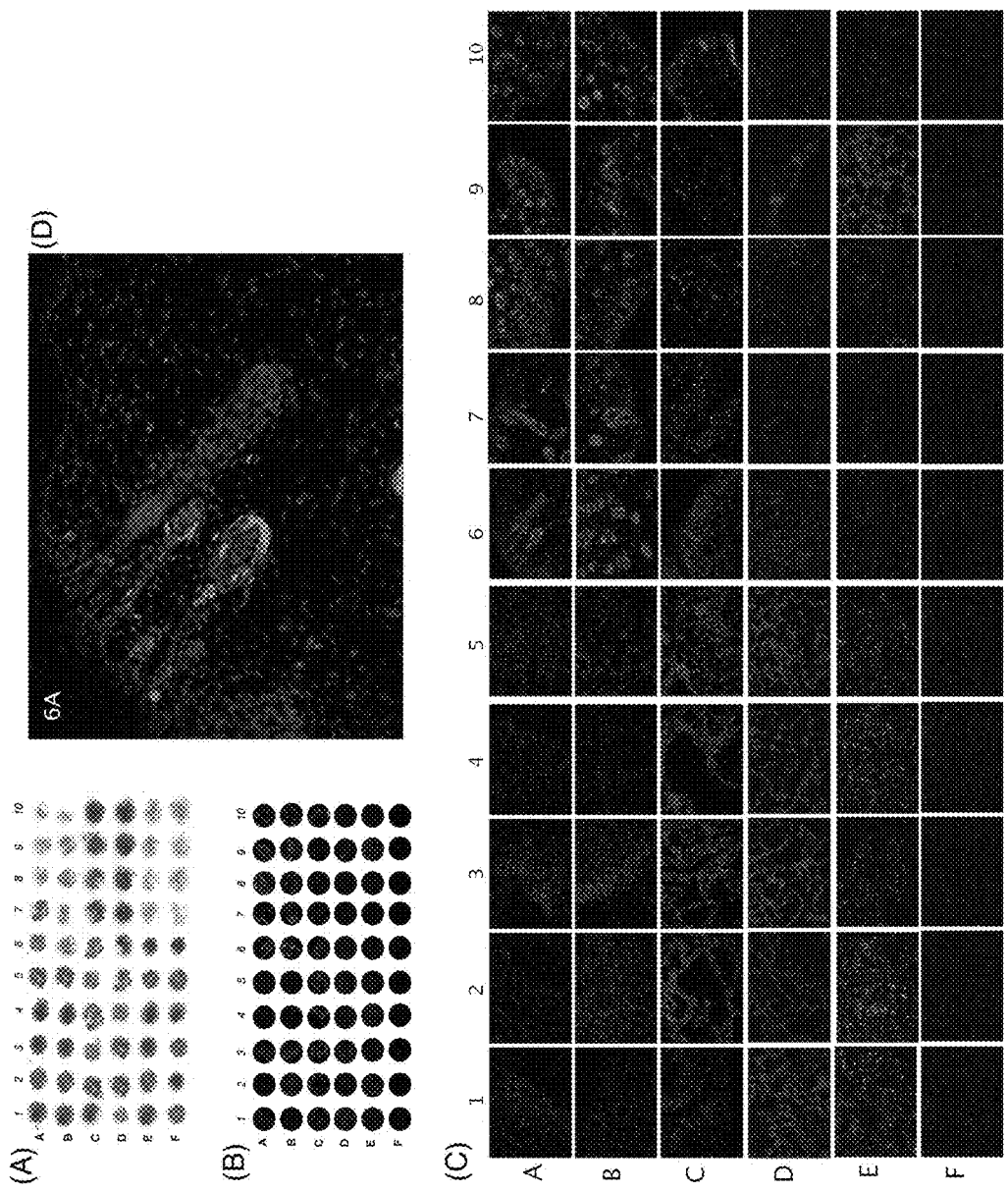
FIG. 11 shows the results of labeling DNA in vivo by using EdU in tissue array. Newborn rats were injected i.p. with 50 μg of EdU per g of body weight in PBS. Major tissues were harvested 7 h later for preparing tissue arrays (Table 3), which were then HE-stained (A) or EdU-stained (B). The EdU-stained tissue array is shown at 20× magnification in panel C. The EdU-labeled skin specimen (6A of panel C) is shown at 200× magnification in panel D. Cellular location was identified by DAPI staining of the nucleus (which would be blue if color photos were used). EdU was detected by Alexa 594 (which would be red if color photos were used).

Pregnant rats were injected i.p. with 200 µg EdU in PBS and the newborn rats were used for the harvest of various tissues at 2 hours, 1 wk and 6 wk after birth. The harvested tissues were fixed in cold 2% formaldehyde and 0.002% saturated picric acid in 0.1 M phosphate buffer, pH 8.0, for 4 hours followed by overnight immersion in buffer containing 30% sucrose. The specimens were then embedded in OCT Compound (Sakura Finetic USA, Torrance, Calif.) and stored at −70° C. until use. Thirty different tissues (Table 3) from both the EdU-injected group and the PBS-injected group were processed for tissue array. Fixed frozen tissue specimens were cut at 10 microns, mounted onto Super-Frost-Plus charged slides (Fisher Scientific, Pittsburgh, Pa.) and air dried for 5 minutes. EdU staining of tissues was performed as described above. The tissues were also stained with hematoxylin and eosin (HE staining) for general histological examination (FIG. 11).

TABLE 3

| | 1 | 2 | 3 | 4 | 5 | 6 | 7 | 8 | 9 | 10 |
|---|---|---|---|---|---|---|---|---|---|---|
| | | | | Tissue array | | | | | | |
| A | Lung | Ovary | Pancreas | Bowel | Heart | Skin | Foreskin | Stomach | Kidney | Bladder |
| B | Lung | Ovary | Pancreas | Bowel | Heart | Skin | Foreskin | Stomach | Kidney | Bladder |
| C | Muscle | Liver | Thymus | Spleen | Brain | Testis | Arm | Penis | Urethra | Fat |
| D | Muscle | Liver | Thymus | Spleen | Brain | Testis | Arm | Penis | Urethra | Fat |
| E | Bladder | Kidney | Penis | Urethra | Testis | Ovary | Stomach | Bowel | Fat | Brain |
| F | Bladder | Kidney | Penis | Urethra | Testis | Ovary | Stomach | Bowel | Fat | Brain |

Note:
A, C, E: EdU injected;
B, D, F: PBS injected

Tracking Transplanted ADSC

Figure 12:
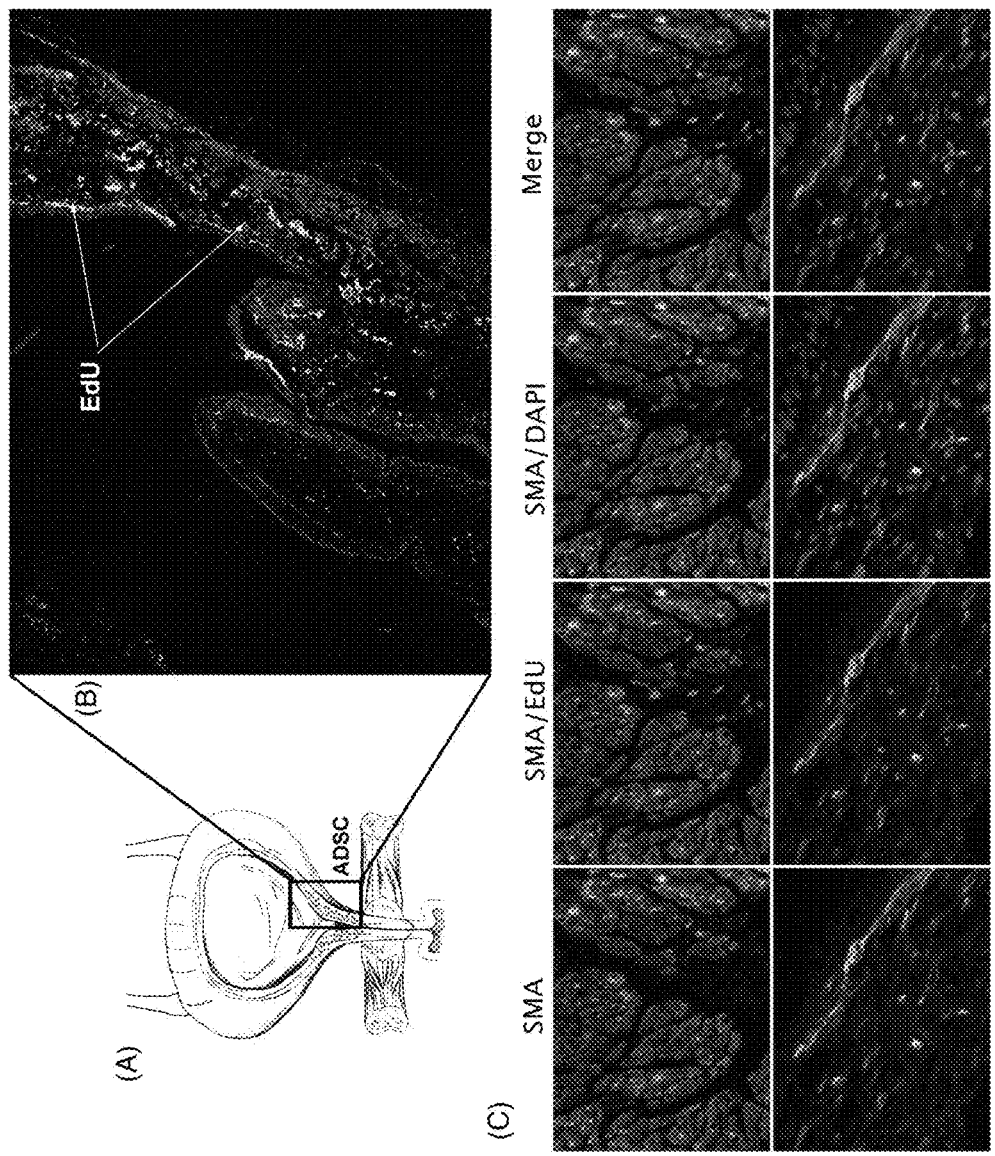
FIG. 12 shows results for tracking transplanted ADSC. Rat ADSC were labeled with 10 μM EdU for 12 hours and then autologously injected into the bladder neck (A). Four weeks later, tissue sections were examined by for EdU (which would be red if color photos were used), alpha-smooth muscle actin (SMA, which would be green if color photos were used), and nucleus (which would be blue if color photos were used). EdU-labeled cells can be seen in the bladder neck (B, ×20). Most EdU-labeled cells were localized in the connective tissue. A few EdU-labeled cells appeared to have differentiated into smooth muscle cells (C, ×200).

A total $1\times10^6$ rat ADSC were labeled with 10 uM EdU for 12 hours and injected autologously to the bladder neck. The tissues were harvested at 1 day, 2 day, 1 week, and 4 weeks post-transplantation. Tissue samples were fixed in cold 2% formaldehyde and 0.002% saturated picric acid in 0.1 M phosphate buffer, pH 8.0, for 4 hours followed by overnight immersion in buffer containing 30% sucrose. The specimens were then embedded in OCT Compound (Sakura Finetic USA, Torrance, Calif.) and stored at −70° C. until use. Fixed frozen tissue specimens were cut at 10 microns, mounted onto SuperFrost-Plus charged slides (Fisher Scientific, Pittsburgh, Pa.) and air dried for 5 minutes. For immunofluorescence examination, the slides were placed in 0.3% $H_2O_2$/methanol for 10 minutes, washed twice in PBS for 5 minutes and incubated with 3% horse serum in PBS/0.3% Triton X-100 for 30 minutes at room temperature. After draining this solution from the tissue section, the slides were incubated at room temperature with anti-alpha smooth muscle actin antibody (Abcam Inc., Cambridge, Mass., 1:500) for 1.5 hours. Control tissue sections were similarly prepared except no primary antibody was added. After rinses, the sections were incubated with FITC-conjugated secondary antibody (Jackson ImmunoResearch Laboratories, West Grove, Pa.). After washing with PBS, the slides were then incubated with fresh made Click-it reaction cocktail for 30 minutes at room temperature without light followed by staining with 4',6-diamidino-2-phenylindole (DAPI, for nuclear staining, 1 µg/ml, Sigma-Aldrich, St. Louis, Mo.). See FIG. 12. Rat ADSC were labeled with 10 µM EdU for 12 hours and then autologously injected into the bladder neck (A). Four weeks later, tissue sections were examined by for EdU (which would be red if color photos were used), alpha-smooth muscle actin (SMA, which would be green if color photos were used), and nucleus (which would be blue if color photos were used). EdU-labeled cells can be seen in the bladder neck (B, ×20). Most EdU-labeled cells were localized in the connective tissue. A few EdU-labeled cells appeared to have differentiated into smooth muscle cells (C, ×200).

Example 14

Treatment of Urinary Incontinence with Syngeneic ADSC

Methods

Twenty-two two-month-old primiparous Sprague-Dawley rats at gestational day 16 were used in this experiment. They were randomly divided into a control group (n=10) and an ADSC-transplanted group (n=12). After parturition, all rats underwent balloon dilation of the vagina and ovariectomy. One week later, the rats received injection of ADSC or PBS.

Syngeneic rat ADSCs were labeled with 10 uM EdU for 12 hours prior to injection. In the treatment group, $1 \times 10^6$ EdU labeled ADSC in 400 µl PBS were injected into the bladder neck and paraurethral tissues. In the control group, 400 µl PBS was injected into the same areas.

Four weeks after injection, all animals underwent assessment of bladder function by conscious cystometry. Cystometry results were classified as "abnormal" if bladder filling was accompanied by frequent, low volume bladder contractions with urethral leakage. Following cystometry, all animals were euthanized. The urethra, vagina, pelvic floor tissue, and bladder were harvested. Immunofluorescent staining of these tissues was performed to localize EdU, alpha smooth muscle actin (SMA), and the nuclei (DAPI staining). Chemical staining was also performed to assess differences in elastic fibers between treatment groups. Statistical analysis was done with Student's t-test.

Results

Figure 13:
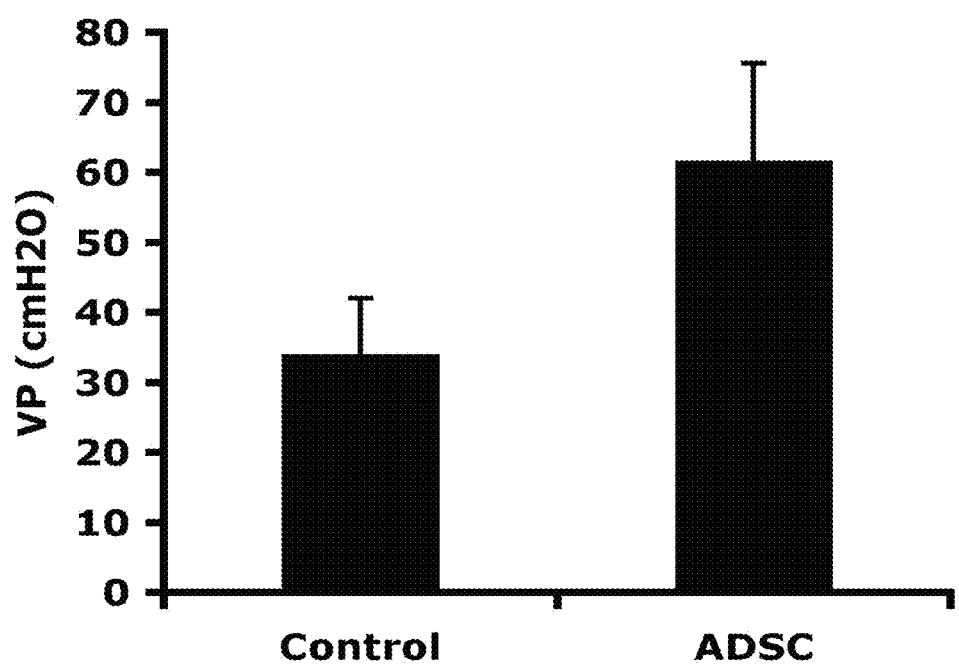
FIG. 13 show the results of experiments on higher voiding pressure in ADSC-treated animals.
Figure 14:
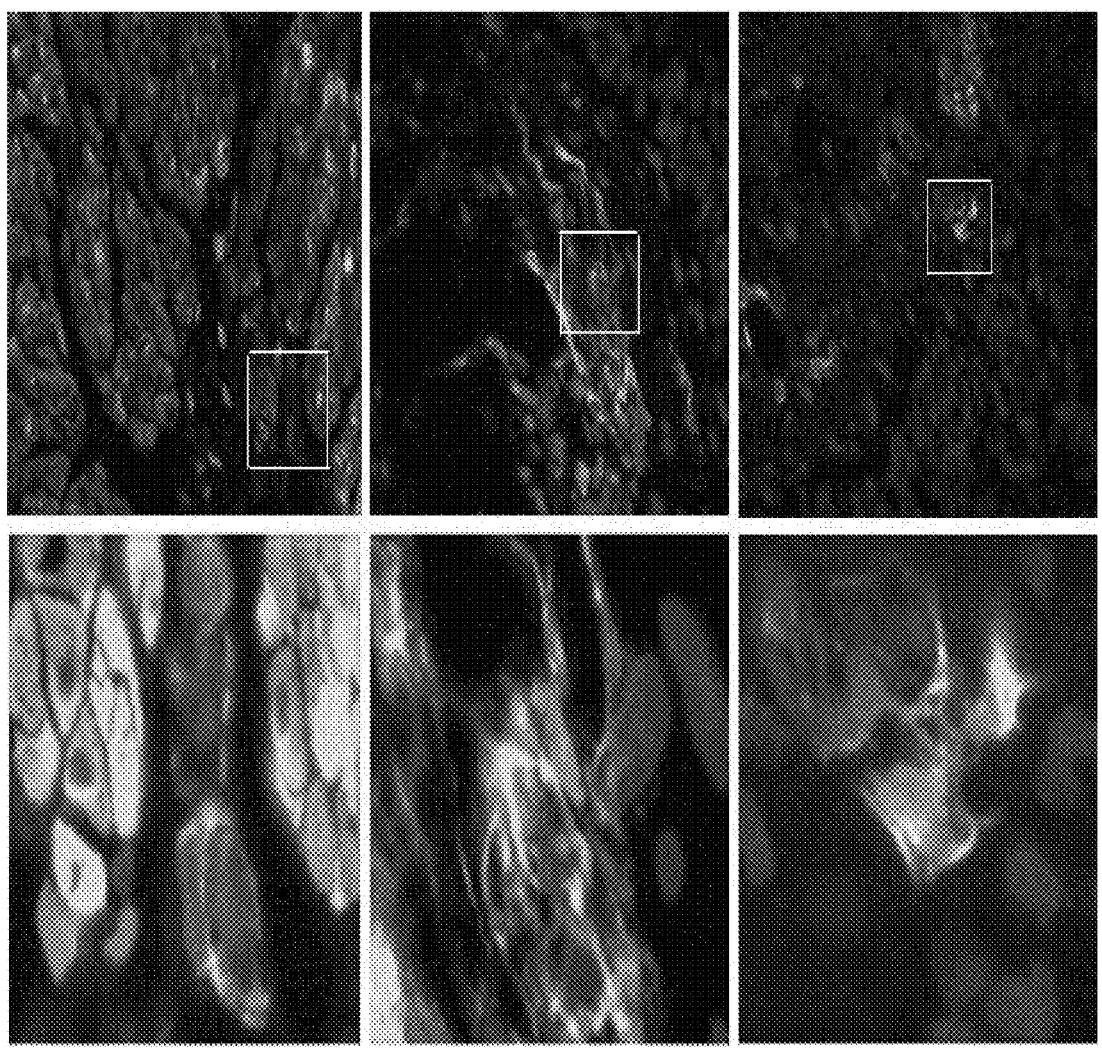
FIG. 14 shows results of co-localization of EdU and SMA. If viewed in color, then the red signal is EdU, the green signal is ASMA, and the blue signal is DAPI. The boxed area in each picture in the upper panels is shown in the corresponding picture in the lower panels (×400).
Figure 15:
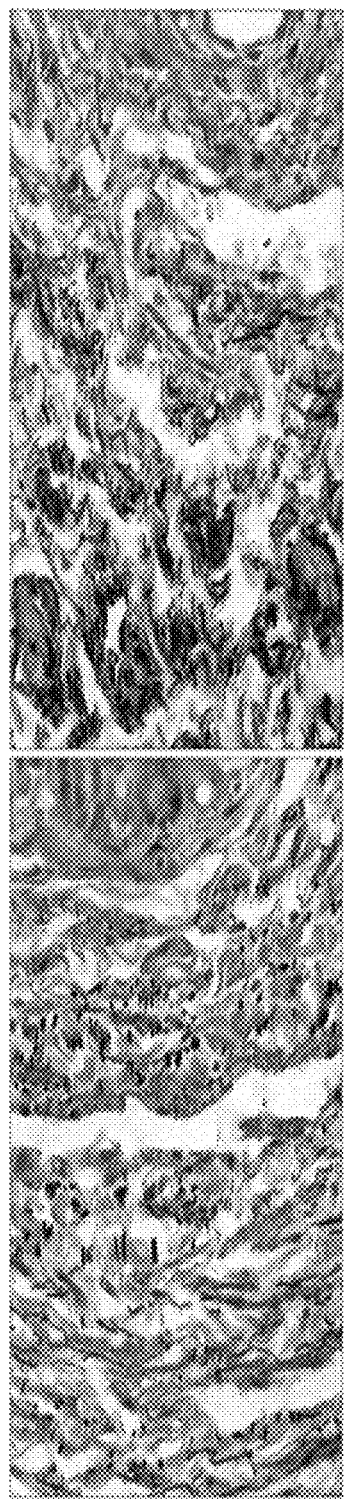
FIG. 15 depicts elastic fibers in the urethra. Left: control. Right: ADSC transplanted (×400).

Based on cystometric criteria described above, 8 out of 10 rats in the control group had abnormal urinary function whereas 4 out of 12 (33.3%) rats in the ADSC treatment group had abnormal urinary function. Mean voiding pressure was significantly higher in the ADSC transplanted group than in the control group (61.7±13.9 cm $H_2O$ vs. 34±8 cm $H_2O$, respectively) (P<0.05) (FIG. 13). EdU-labeled cells were identified in the submucosa of bladder neck and urethra. Some of these EdU-positive cells were also positive for SMA, suggesting differentiation of ADSC into smooth muscle cells (FIG. 14). There were significantly more elastic fibers in the urethra of rats treated with ADSC (FIG. 15).

Example 15

Treatment of Urinary Incontinence with Xenogeneic ADSC

Methods

Twelve two-month-old primiparous Sprague-Dawley rats at gestational day 16 were used in this experiment. They were randomly divided into a control group (n=5) and an ADSC-transplanted group (n=7). After parturition, all rats underwent balloon dilation of the vagina and ovariectomy. One week later, the rats received injection of ADSC or PBS.

ADSC were isolated from a 1-month-old male Yorkshire pig and labeled with 10 uM EdU for 12 hours prior to injection. In the treatment group, $1 \times 10^6$ EdU labeled ADSC in 400 ul PBS were injected into the bladder neck and paraurethral tissues. In the control group, 400 ul PBS was injected into the same areas.

Four weeks after injection, all animals underwent assessment of bladder function by conscious cystometry. Cystometry results were classified as "abnormal" if bladder filling was accompanied by frequent, low volume bladder contractions with urethral leakage. Following cystometry, all animals were euthanized. The urethra, vagina, pelvic floor tissue, and bladder were harvested. Immunofluorescent staining of these tissues was performed to localize EdU, alpha smooth muscle actin (SMA), and the nuclei (DAPI staining). Chemical staining was also performed to assess differences in elastic fibers between treatment groups. Statistical analysis was done with Student's t-test.

Results

Figure 16:
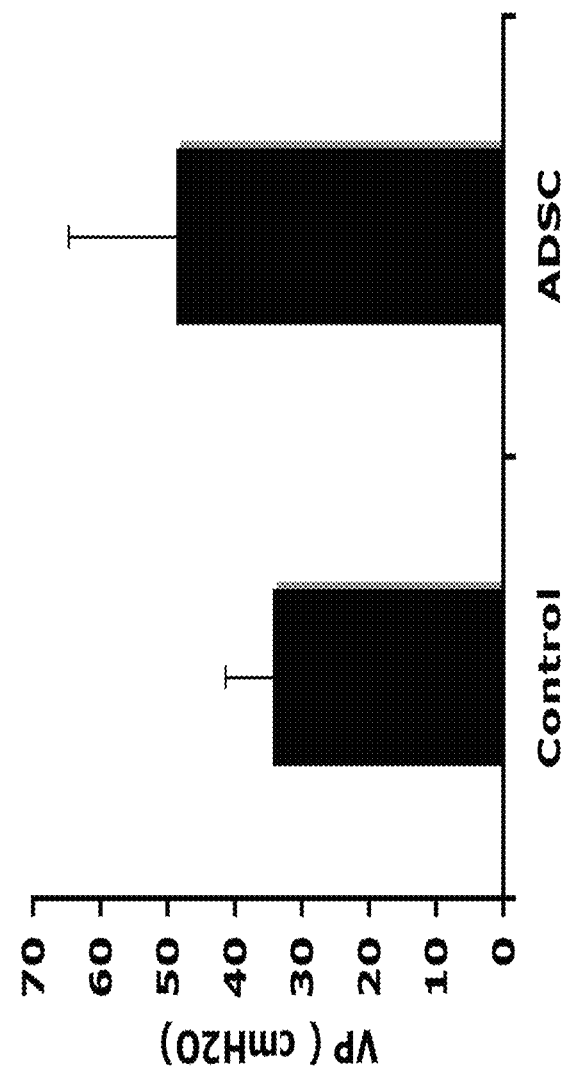
FIG. 16 shows the results of experiments on higher voiding pressure in ADSC-treated animals.
Figure 17:
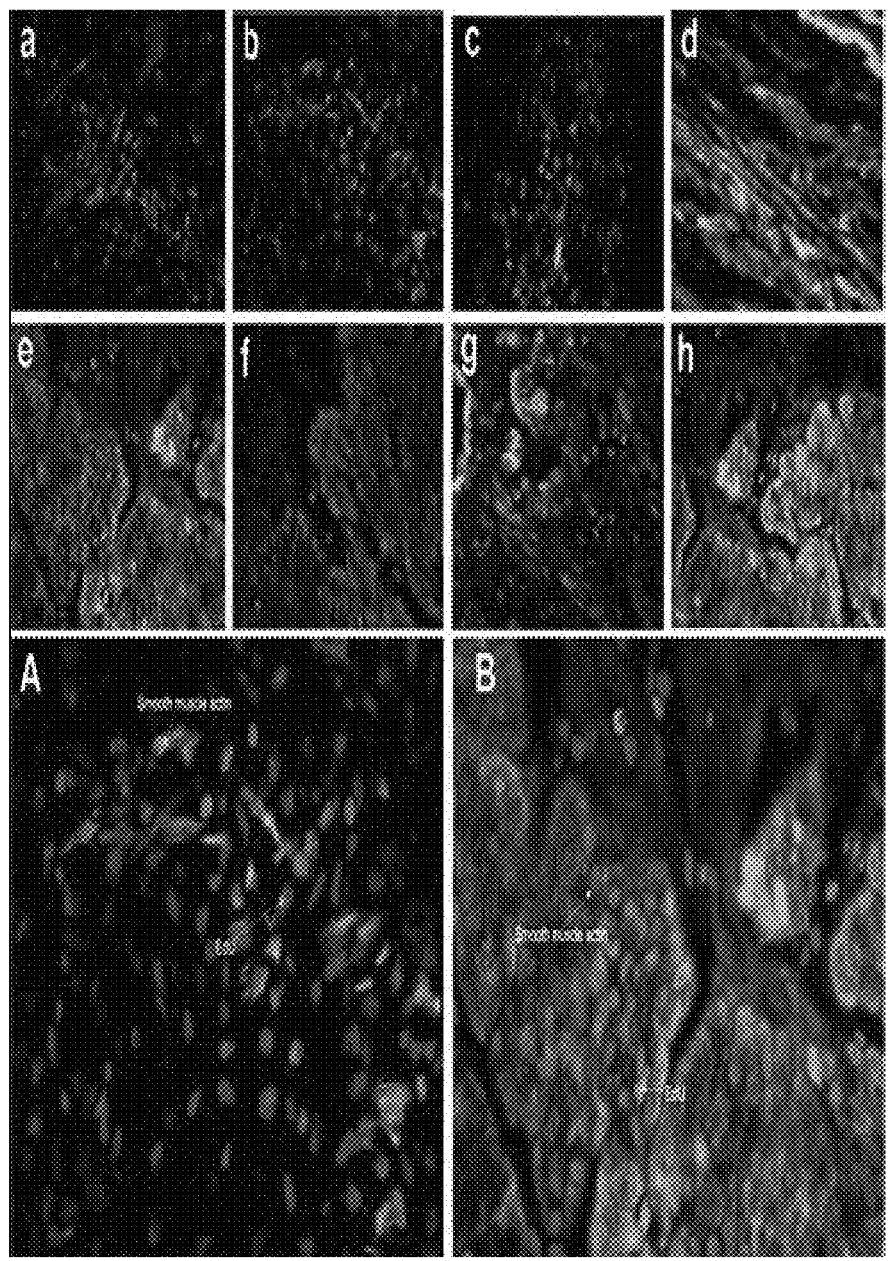
FIG. 17 shows experiments on co-localization of EdU and SMA. If viewed in color, then the red signal is EdU, the green signal is ASMA, and the blue signal is DAPI. (a-c) EdU positive cells localized in submucosa. (d-h) EdU positive cells localized in muscle (×200). (A) EdU positive cells in submucosa (×400). (B) EdU positive cells in muscle (×400).

Based on cystometric criteria described above, 4 out of 5 rats in the control group had abnormal urinary function whereas 1 out of 7 (14.2%) rats in the ADSC treatment group had abnormal urinary function. Mean voiding pressure was higher in the ADSC transplanted group than in the control group (48.7±16.1 cm $H_2O$ vs. 34.4±7.8 cm $H_2O$, respectively) (P=0.097) (FIG. 16). EdU-labeled cells were identified in the submucosa of bladder neck and urethra. Some of these EdU-positive cells were also positive for SMA, suggesting differentiation of ADSC into smooth muscle cells (FIG. 17).

Example 16

Endothelial Differentiation of ADSC

In Vivo Endothelial Differentiation

Figure 18:
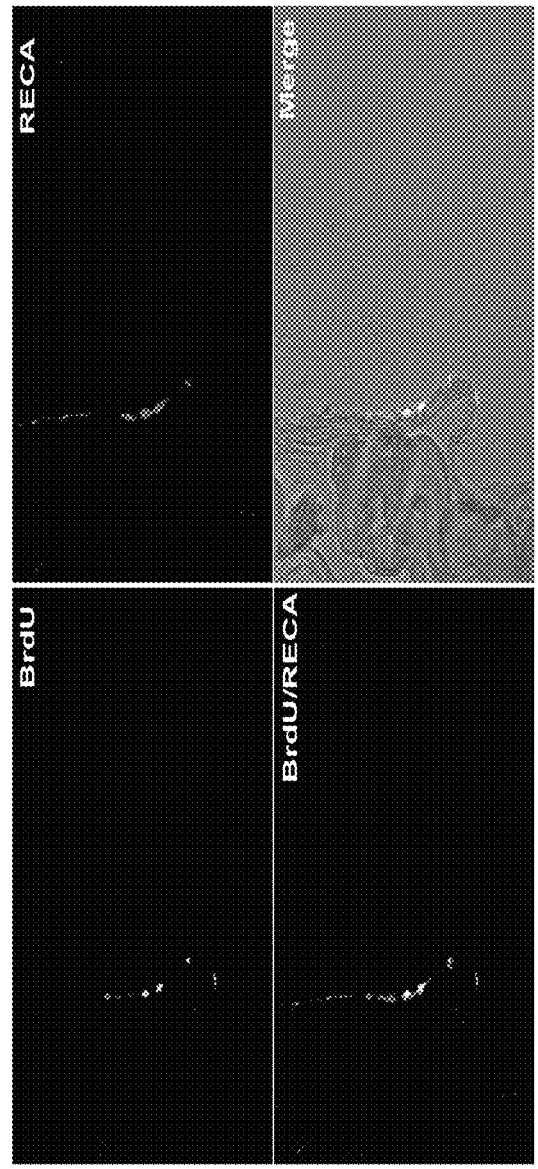
FIG. 18 shows results of experiments on endothelial differentiation of ADSC in the penis. ADSC were labeled with BrdU and injected into the corpus cavernosa of rats. Four weeks later the tissues were examined by immunofluorescence microscopy. Anti-BrdU and RECA-1 antibodies identified the injected ADSC (which would be green if color photos were used) and endothelial cells (which would be red if color photos were used), respectively. Superimposed image (BrdU/RECA) shows that some ADSC (which would be yellow if color photos were used) also stained positive for RECA-1. Another superimposed image (Merge) with the phase-contrast image shows the localization of ADSC to the sinusoid endothelium. Approximately 5% of BrdU+ cells were RECA+, as determined by counting 10 randomly selected areas in the cross section.

To test whether ADSC could differentiate into endothelial cells, we injected ADSC into the penis of rats and examined the tissue 4 weeks later. ADSC were identified by BrdU staining, and approximately 5% of them also stained positive for rat endothelial cell antigen (RECA-1). These cells were localized to the sinusoid endothelium as revealed by the superimposed images of fluorescence and phase-contrast microscopy (FIG. 18).

Morphology and Growth Characteristics of Cells Grown in EGM2 Medium

Figure 19:
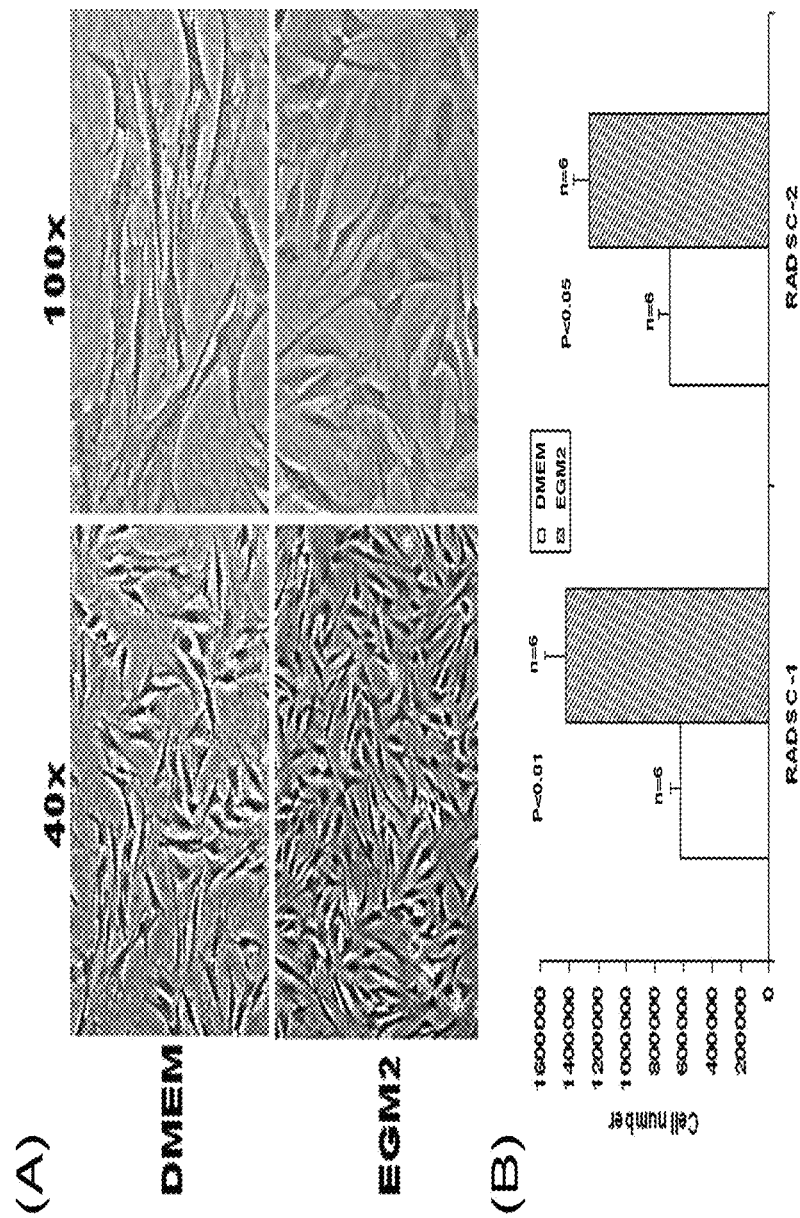
FIG. 19 shows a comparison of cell morphology and growth rate in DMEM and EGM2. Two rat ADSC lines, RADSC-1 and RADSC-2, were seeded into 100-mm dishes at identical density (300,000 cells/dish) and grown for 3 days in DMEM or EGM2. The cell morphology of RADSC-1 is shown in panel A. The growth rate of both cell lines is shown in panel B.

ADSC were routinely cultured in DMEM. Endothelial cells were routinely cultured in EGM2, which is a commercially available endothelial growth medium. When DMEM in ADSC cultures was replaced with EGM2, the cells reached confluence faster and appeared more compact (larger nuclei) than cells that remained in DMEM. Proliferation assay confirmed that ADSC grew much more rapidly in EGM2 than in DMEM (FIG. 19).

Endothelial Characteristics

Figure 20:
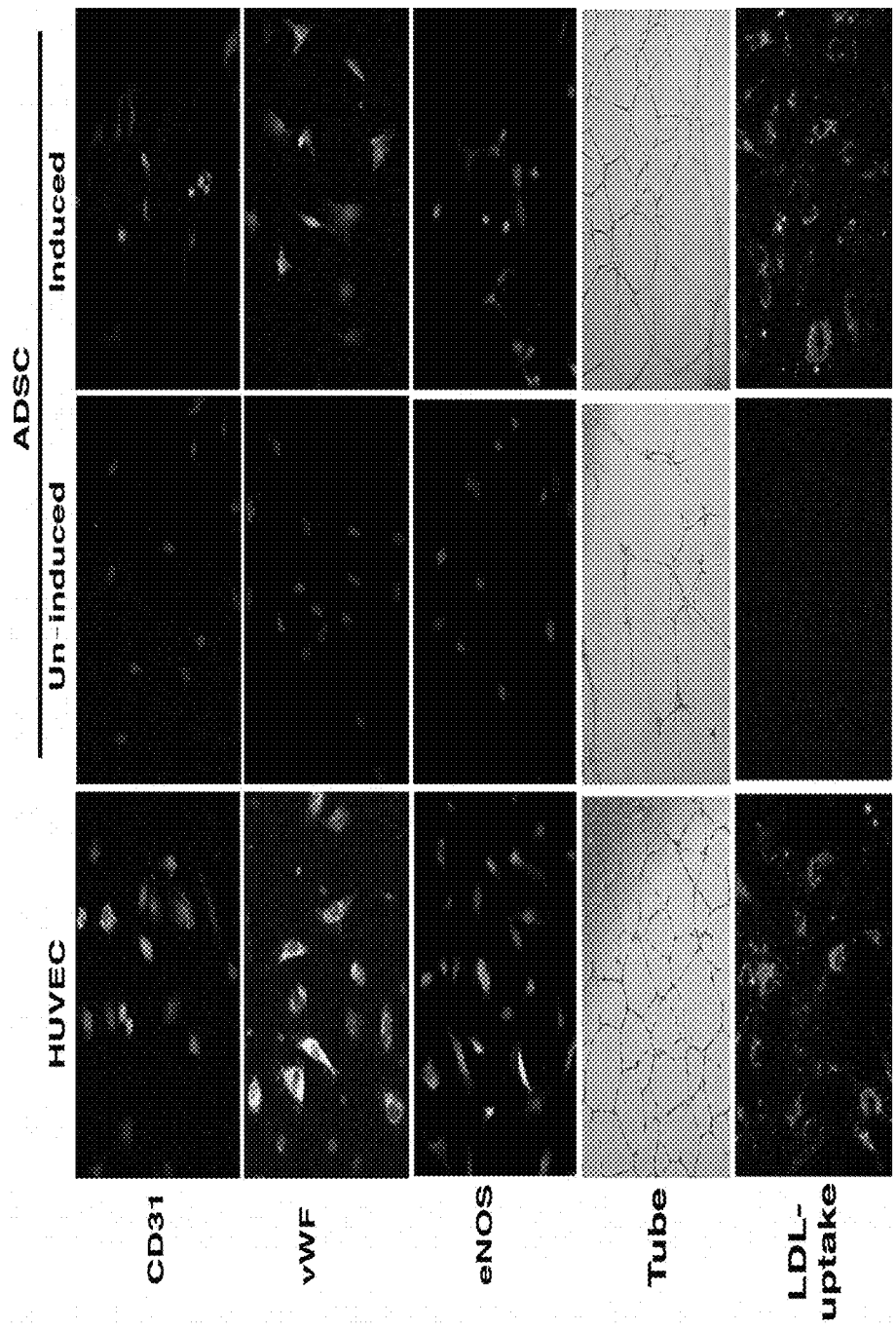
FIG. 20 show the results of experiments to identify the expression of endothelial markers in cells grown in EGM2. RADSC-1 and RADSC-2 were grown in DMEM (un-induced) or EGM2 (induced). They were then stained for endothelial markers CD31, vWF, and eNOS. If viewed in color, then the green indicates expression of CD31, vWF, or eNOS; the blue color indicates cell nuclei. Original magnification was 200×. The cells were also assayed for Matrigel tube formation (Tube) and LDL-uptake. The red color indicates the presence of LDL, which was in a conjugated form with the red fluorescence dye DiI. The results were similar for both cell lines; only those of RADSC-1 are shown. Human umbilical vein endothelial cells (HUVEC) served as positive control. Experiments were repeated 3 times.

Immunocytochemistry showed that ADSC grown in EGM2 expressed endothelial specific markers CD31, vWF, and eNOS (FIG. 20). Matrigel tube formation assay also showed that ADSC grown in EGM2 were able to form endothelial-like tube structures. Additionally, LDL uptake assay showed that ADSC grown in EGM2 were capable of LDL uptake. The endothelial specificity of these three assays was supported by positive results with HUVEC cells.

Reversibility and Re-Inducibility of Endothelial Differentiation

Figure 21:
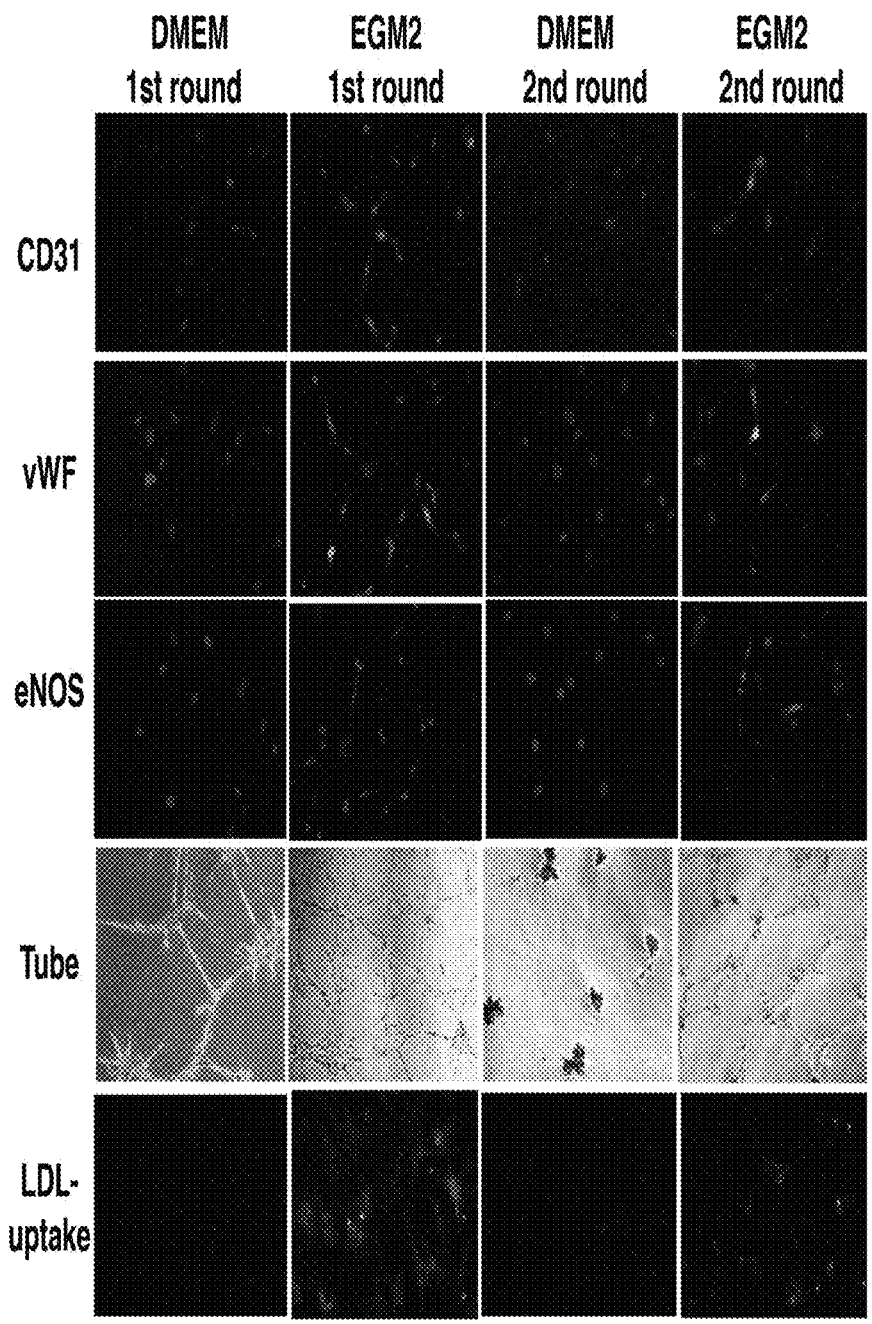
FIG. 21 shows some results that illustrate the reversibility and re-inducibility of endothelial differentiation. RADSC-1 and RADSC-2 were grown in DMEM for 6-10 days (DMEM 1st round); half of the cells were assayed for endothelial markers. The other half of the cells were switched to EGM2, grown for 6 days (first round EGM2), and half of the cells were assayed for endothelial markers. The other half of the cells were switched to DMEM, grown for 10 days (2nd round DMEM), and half of the cells were assayed for endothelial markers. Finally, the other half of the cells were switched to EGM2, grown for 6 days (2nd round EGM2), and assayed for endothelial markers. The results were similar for both cell lines; only those of RADSC-1 are shown. If viewed in color, then the green indicates expression of CD31, vWF, or eNOS; and the blue color indicates cell nuclei. Original magnification was 200×. The red color indicates the presence of LDL, which was in a conjugated form with the red fluorescence dye DiI. Experiments were repeated 3 times.

Whether ADSC differentiation is reversible was tested by replacing EGM2 with DMEM. This resulted in the disappearance of all endothelial characteristics (FIG. 21). Whether endothelial differentiation can be re-induced was tested by reintroducing EGM2 to the cells. This resulted in the reappearance of all endothelial characteristics, albeit at reduced levels. These tests established that the EGM2 medium contains specific factors capable of inducing ADSC endothelial differentiation.

Identification of Endothelial-Inducing Factors

Figure 22:
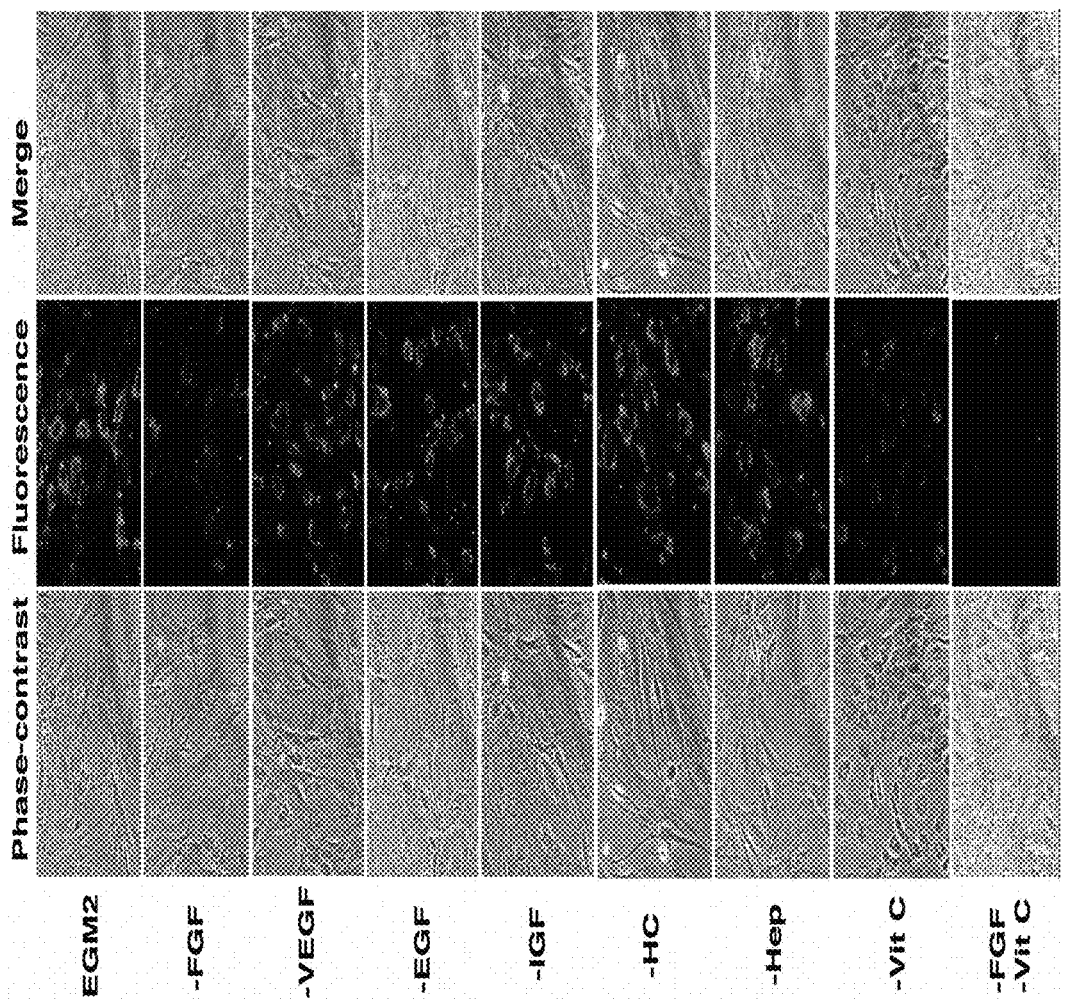
FIG. 22 shows results of experiments on the identification of endothelial-inducing factor by "subtraction." RADSC-1 cells were grown in fully or partially supplemented EGM2 and then assayed for LDL-uptake. Each partially supplemented EGM2 is indicated by the omitted factor; for example, "-FGF" denotes EGM2 without FGF2. Experiments were repeated 3 times.
Figure 23:
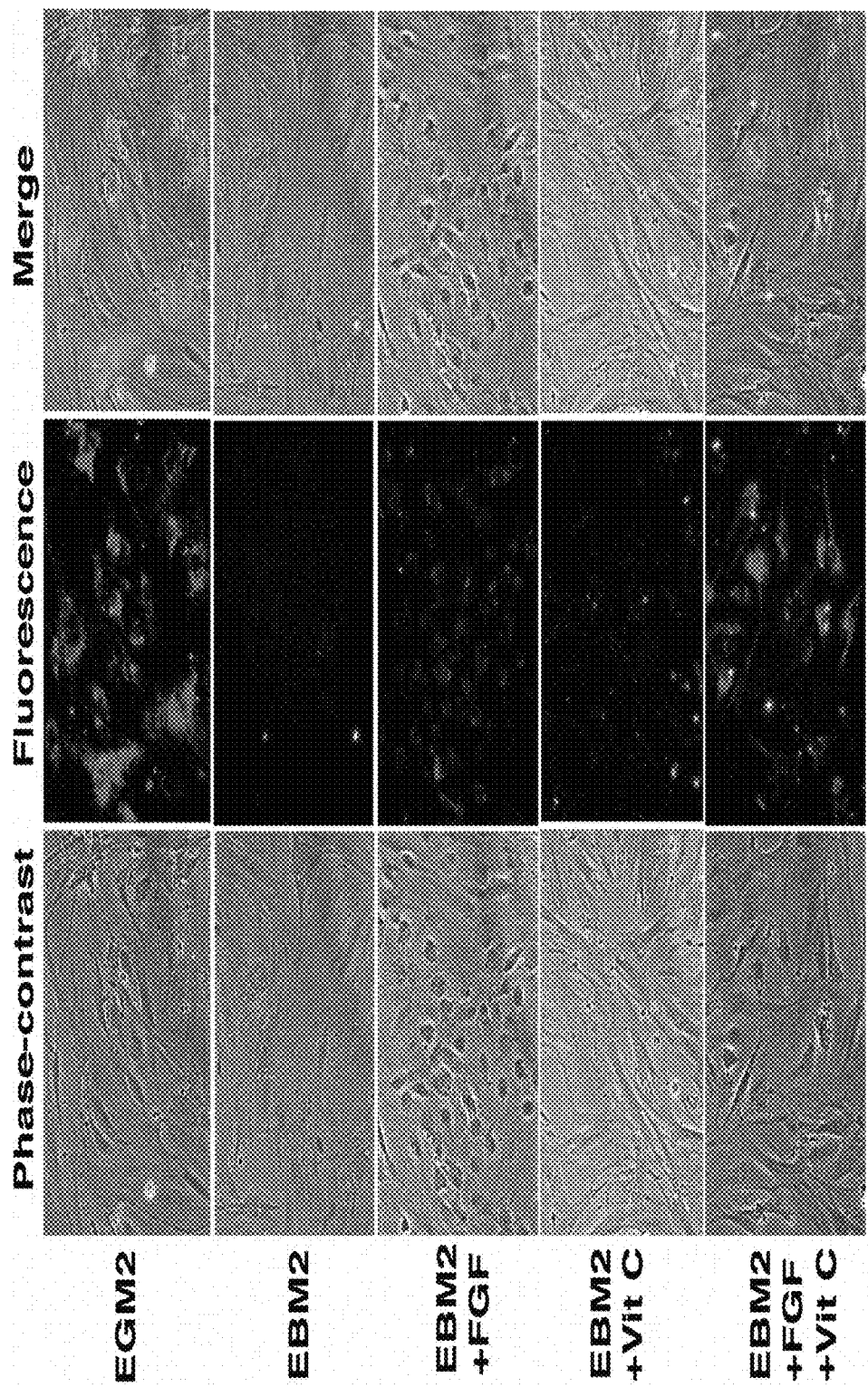
FIG. 23 shows results of experiments on the identification of endothelial-inducing factor by "addition." RADSC-1 cells were grown in EGM2, EBM2, or EBM2 supplemented with the indicated factor, and then assayed for LDL-uptake. Experiments were repeated 3 times.

EGM2 medium is supplied by the manufacturer in the form of a basal medium (EBM2) and individual vials of supplemental factors. This packaging format allowed us to test the importance of each supplemental factor as related to ADSC endothelial differentiation. Specifically, we prepared "subtraction" EGM2 media by omitting one supplemental factor at a time. We then maintained ADSC in each subtracted EGM2 medium for one week and then assayed for their LDL-uptake ability, which has been shown to be the most reliable endothelial marker. The results show that, among growth factors, the omission of VEGF, EGF, or IGF had essentially no effect, whereas the omission of FGF2 greatly diminished ADSC's LDL-uptake ability (FIG. 22). Among non-growth factors, the omission of hydrocortisone or heparin had essentially no effect, whereas the omission of vitamin C greatly diminished ADSC's LDL-uptake ability. When both FGF2 and vitamin C were omitted, ADSC exhibited essentially no LDL-uptake ability. To further confirm the importance of FGF2 and vitamin C, we prepared "addition" media by adding FGF2 and/or vitamin C to EBM2, maintained ADSC in these media for one week, and then assayed ADSC's LDL-uptake ability. The results show that (1) EBM2 supplemented with FGF2 and vitamin C was nearly as effective as EGM2, (2) EBM2 supplemented with FGF2 was still effective, albeit at a reduced level, and (3) EBM2 supplemented with vitamin C was still somewhat effective, but at a much reduced level (FIG. 23). It is also noteworthy that cells grown in EGM2 without vitamin C (FIG. 22) or in FGF2-supplemented EBM2 (FIG. 23) assumed a round-shape morphology, which may be indicative of oxidative stress.

Induction of Other Endothelial Characteristics by FGF2

Figure 24:
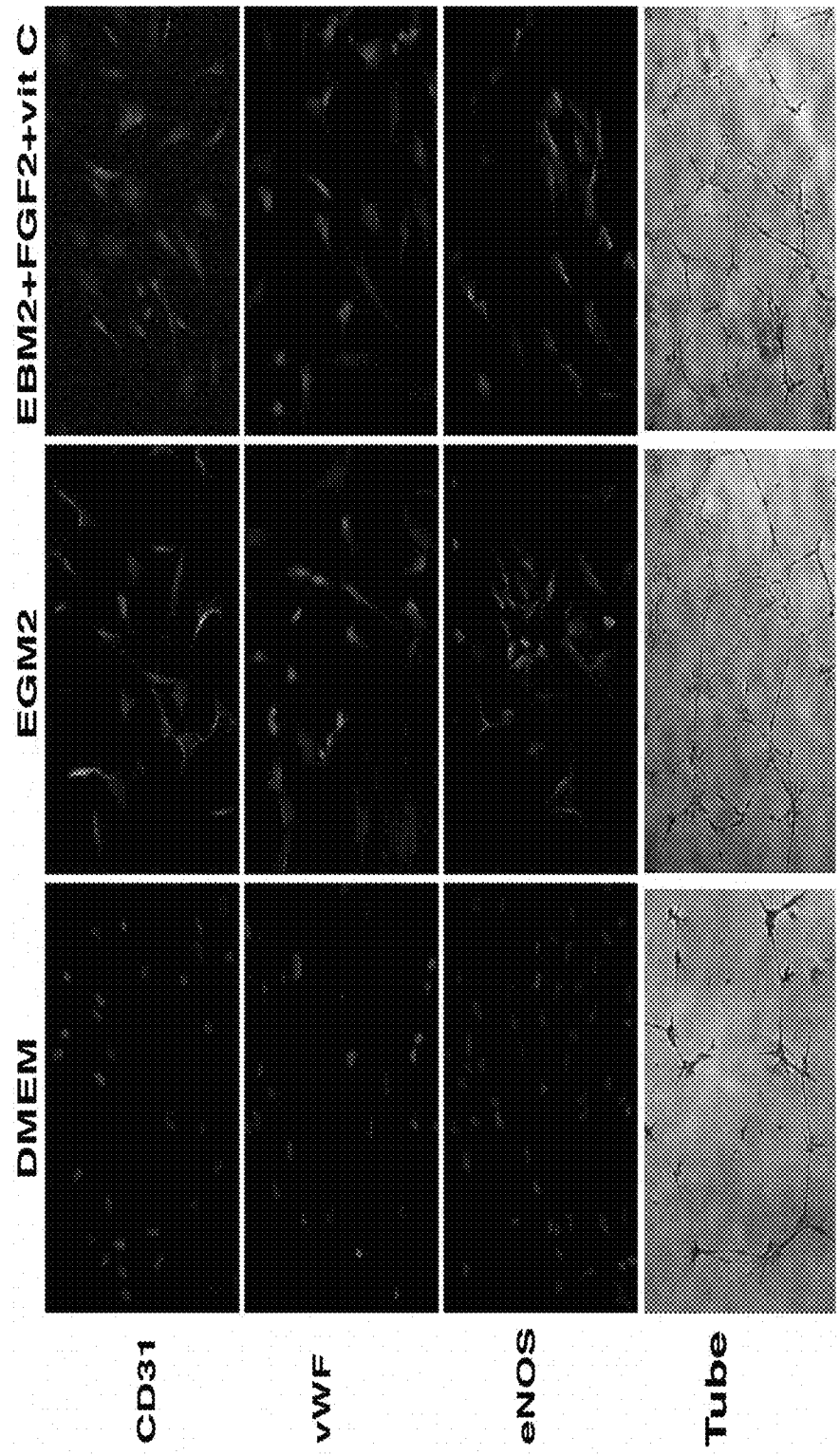
FIG. 24 shows results of experiments on the induction of endothelial marker expression by FGF2. RADSC-1 cells were grown in DMEM, EGM2, or EBM2 supplemented with FGF2 and vitamin C. They were then stained for endothelial markers CD31, vWF, and eNOS. If viewed in color, then the green indicates expression of CD31, vWF, or eNOS; and the blue indicates cell nuclei. Original magnification was 200×. The cells were also assayed for Matrigel tube formation (Tube). Experiments were repeated 3 times.

The above experiments identified FGF2 as the only growth factor required for the induction of ADSC's LDL-uptake ability. We then tested whether FGF2 was able to induce the expression of additional endothelial characteristics. The results show that indeed this was the case; that is, cells grown in FGF2/vitamin C-supplemented EBM2 acquired all of the tested endothelial markers, as did cells grown in the completely supplemented EGM2 (FIG. 24).

FGFR1 Inhibitor Blocks ADSC Endothelial Differentiation

To further confirm the critical role of FGF2 in ADSC endothelial differentiation, we conducted ADSC differentiation experiments in the presence or absence of PD173074, a selective inhibitor for FGF receptor (FGFR1). In the absence of PD173074 (with the addition of solvent only), cells grown in either the completely supplemented EGM2 or the FGF2/vitamin C-supplemented EBM2 acquired the LDL-uptake ability (FIG. 25). On the other hand, in the presence of PD173074, cells grown in either medium were unable to do so (FIG. 25). To ensure that VEGF signaling did not interfere with this test, as PD173074 is known to have a weaker inhibitory action on VEGF receptor (VEGFR2), we showed that ADSC grown in VEGF/vitamin C-supplemented EBM2 did not acquire the LDL-uptake ability.

What is claimed is:

1. A method of treating a medical condition in a non-human mammal in need thereof comprising administering to the non-human mammal an effective amount of a purified population of porcine adipose tissue-derived stem cells (ADSC),
    wherein the medical condition is one or more condition selected from the group consisting of: tissue regeneration, scarring, soft tissue defect, fecal incontinence, dilated cardiomyopathy, hip dysplasia, avascular necrosis of the femoral head, spinal cord injury, atherosclerosis-related infarctions, muscular dystrophy, and pain, and wherein the ADSC are xenogenic to the non-human mammal.

2. The method of claim 1, wherein the non-human mammal is selected from the group consisting of dog, cat, horse, rabbit, monkey, baboon, chimpanzee, orangutan, tiger, lion, bear, cheetah, and llama.

3. The method of claim 1 wherein the effective amount of ADSC is within in the range of $0.05 \times 10^6$ to $100 \times 10^6$ ADSC.

4. The method of claim 3 wherein the effective amount of ADSC is within in the range of $1 \times 10^6$ to $10^7$ ADSC.

5. The method of claim 1 wherein the effective amount of ADSC is $0.5 \times 10^6$ ADSC/kg of body weight of the non-human mammal.

6. The method of claim 1 wherein the purified population is with the range of 60% to 99% pure.

7. The method of claim 6 wherein the purified population is with the range of 80% to 99% pure.

8. The method of claim 7 wherein the purified population is with the range of 90% to 99% pure.

9. The method of claim 1, wherein the effective amount is delivered by intravenous administration.

10. The method of claim 1, comprising delivery of a composition comprising the effective amount of the purified population of porcine adipose tissue-derived ADSC and at least one of a pharmaceutically acceptable carrier, excipient, adjuvant, or diluent.

11. The method of claim 10, wherein the pharmaceutically acceptable carrier, excipient, adjuvant, or diluent is chemically inert to the effective amount of the purified population of porcine adipose tissue-derived ADSC.

* * * * *